US008052749B2

(12) United States Patent
Salahieh et al.

(10) Patent No.: US 8,052,749 B2
(45) Date of Patent: Nov. 8, 2011

(54) METHODS AND APPARATUS FOR ENDOVASCULAR HEART VALVE REPLACEMENT COMPRISING TISSUE GRASPING ELEMENTS

(75) Inventors: Amr Salahieh, Saratoga, CA (US); Daniel Hildebrand, Menlo Park, CA (US); Tom Saul, El Granada, CA (US)

(73) Assignee: Sadra Medical, Inc., Los Gatos, CA (US)

(*) Notice: Subject to any disclaimer, the term of this patent is extended or adjusted under 35 U.S.C. 154(b) by 806 days.

(21) Appl. No.: 11/232,444

(22) Filed: Sep. 20, 2005

(65) Prior Publication Data

US 2006/0058872 A1    Mar. 16, 2006

Related U.S. Application Data

(63) Continuation-in-part of application No. 10/972,287, filed on Oct. 21, 2004, which is a continuation-in-part of application No. 10/746,240, filed on Dec. 23, 2003, now abandoned.

(51) Int. Cl.
*A61F 2/24* (2006.01)
(52) U.S. Cl. .................. 623/2.17; 623/2.12; 623/1.26
(58) Field of Classification Search .............. 623/1.24, 623/1.26, 2.1–2.19, 2.38, 1.31
See application file for complete search history.

(56) References Cited

U.S. PATENT DOCUMENTS

| 0,015,192 A | 6/1856 | Peale |
| 2,682,057 A | 6/1954 | Lord |
| 2,701,559 A | 2/1955 | Cooper |
| 2,832,078 A | 4/1958 | Williams |
| 3,099,016 A | 7/1963 | Edwards |
| 3,113,586 A | 12/1963 | Edmark, Jr. |
| 3,130,418 A | 4/1964 | Head et al. |
| 3,143,742 A | 8/1964 | Cromie |
| 3,334,629 A | 8/1967 | Cohn |
| 3,367,364 A | 2/1968 | Cruz, Jr. et al. |
| 3,409,013 A | 11/1968 | Berry |
| 3,445,916 A | 5/1969 | Schulte |
| 3,540,431 A | 11/1970 | Mobin-Uddin |
| 3,548,417 A | 12/1970 | Kischer |
| 3,570,014 A | 3/1971 | Hancock |
| 3,587,115 A | 6/1971 | Shiley |
| 3,592,184 A | 7/1971 | Watkins |
| 3,628,535 A | 12/1971 | Ostrowsky et al. |

(Continued)

FOREIGN PATENT DOCUMENTS

CN    1338951    3/2002

(Continued)

OTHER PUBLICATIONS

Salahieh, et al., U.S. Appl. No. 11/531,980, "Externally expandable heart valve anchor and method," filed Sep. 14, 2006.

(Continued)

*Primary Examiner* — Thomas J Sweet
*Assistant Examiner* — Rebecca Straszheim
(74) *Attorney, Agent, or Firm* — Vidas, Arrett & Steinkraus

(57) ABSTRACT

The present invention provides an apparatus for endovascularly replacing a patient's heart valve. In some embodiments, the apparatus includes an expandable anchor supporting a replacement valve, the anchor and replacement valve being adapted for percutaneous delivery and deployment to replace the patient's heart valve, the anchor having a braid having atraumatic grasping elements adapted to grasp tissue in a vicinity of the patient's heart valve.

9 Claims, 38 Drawing Sheets

U.S. PATENT DOCUMENTS

| | | |
|---|---|---|
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,997,923 A | 12/1976 | Possis |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos et al. |
| 4,291,420 A | 9/1981 | Reul |
| 4,297,749 A | 11/1981 | Davis et al. |
| 4,323,358 A | 4/1982 | Lentz et al. |
| 4,326,306 A | 4/1982 | Poler |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,423,809 A | 1/1984 | Mazzocco |
| 4,425,908 A | 1/1984 | Simon |
| 4,470,157 A | 9/1984 | Love |
| 4,484,579 A | 11/1984 | Meno et al. |
| 4,501,030 A | 2/1985 | Lane |
| 4,535,483 A | 8/1985 | Klawitter et al. |
| 4,574,803 A | 3/1986 | Storz |
| 4,580,568 A | 4/1986 | Gianturco |
| 4,602,911 A | 7/1986 | Ahmadi et al. |
| 4,605,407 A | 8/1986 | Black et al. |
| 4,610,688 A | 9/1986 | Silvestrini et al. |
| 4,612,011 A | 9/1986 | Kautzky |
| 4,617,932 A | 10/1986 | Kornberg |
| 4,643,732 A | 2/1987 | Pietsch et al. |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | DiPisa, Jr. |
| 4,665,906 A | 5/1987 | Jervis |
| 4,680,031 A | 7/1987 | Alonso |
| 4,692,164 A | 9/1987 | Dzemeshkevich et al. |
| 4,705,516 A | 11/1987 | Barone et al. |
| 4,710,192 A | 12/1987 | Liotta et al. |
| 4,733,665 A | 3/1988 | Palmaz |
| 4,755,181 A | 7/1988 | Igoe |
| 4,759,758 A | 7/1988 | Gabbay |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,829,990 A | 5/1989 | Thuroff et al. |
| 4,834,755 A | 5/1989 | Silvestrini et al. |
| 4,851,001 A | 7/1989 | Taheri |
| 4,856,516 A | 8/1989 | Hillstead |
| 4,865,600 A | 9/1989 | Carpentier et al. |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,885,005 A | 12/1989 | Nashef et al. |
| 4,909,252 A | 3/1990 | Goldberger |
| 4,917,102 A | 4/1990 | Miller et al. |
| 4,922,905 A | 5/1990 | Strecker |
| 4,954,126 A | 9/1990 | Wallsten |
| 4,966,604 A | 10/1990 | Reiss |
| 4,969,890 A | 11/1990 | Sugita et al. |
| 4,979,939 A | 12/1990 | Shiber |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,132,473 A | 7/1992 | Furutaka et al. |
| 5,141,494 A | 8/1992 | Danforth et al. |
| 5,152,771 A | 10/1992 | Sabbaghian et al. |
| 5,159,937 A | 11/1992 | Tremulis |
| 5,161,547 A | 11/1992 | Tower |
| 5,163,953 A | 11/1992 | Vince |
| 5,167,628 A | 12/1992 | Boyles |
| 5,209,741 A | 5/1993 | Spaeth |
| 5,215,541 A | 6/1993 | Nashef et al. |
| 5,217,483 A | 6/1993 | Tower |
| 5,258,042 A | 11/1993 | Mehta |
| 5,282,847 A | 2/1994 | Trescony et al. |
| 5,295,958 A | 3/1994 | Shturman |
| 5,332,402 A | 7/1994 | Teitelbaum |
| 5,336,258 A | 8/1994 | Quintero et al. |
| 5,350,398 A | 9/1994 | Pavcnik et al. |
| 5,360,444 A | 11/1994 | Kusuhara |
| 5,370,685 A | 12/1994 | Stevens |
| 5,389,106 A | 2/1995 | Tower |
| 5,397,351 A | 3/1995 | Pavcnik et al. |
| 5,409,019 A | 4/1995 | Wilk |
| 5,411,552 A | 5/1995 | Andersen et al. |
| 5,425,762 A | 6/1995 | Muller |
| 5,431,676 A | 7/1995 | Dubrul et al. |
| 5,443,446 A | 8/1995 | Shturman |
| 5,443,495 A | 8/1995 | Buscemi et al. |
| 5,443,499 A | 8/1995 | Schmitt |
| 5,476,506 A | 12/1995 | Lunn |
| 5,476,510 A | 12/1995 | Eberhardt et al. |
| 5,480,423 A | 1/1996 | Ravenscroft et al. |
| 5,480,424 A | 1/1996 | Cox |
| 5,500,014 A | 3/1996 | Quijano et al. |
| 5,507,767 A | 4/1996 | Maeda et al. |
| 5,534,007 A | 7/1996 | St. Germain et al. |
| 5,545,133 A | 8/1996 | Burns et al. |
| 5,545,209 A | 8/1996 | Roberts et al. |
| 5,545,211 A | 8/1996 | An et al. |
| 5,549,665 A | 8/1996 | Vesely et al. |
| 5,554,185 A | 9/1996 | Block et al. |
| 5,571,175 A | 11/1996 | Vanney et al. |
| 5,571,215 A | 11/1996 | Sterman et al. |
| 5,575,818 A | 11/1996 | Pinchuk |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,645,559 A | 7/1997 | Hachtman et al. |
| 5,662,671 A | 9/1997 | Barbut et al. |
| 5,667,523 A | 9/1997 | Bynon et al. |
| 5,674,277 A | 10/1997 | Freitag |
| 5,693,083 A | 12/1997 | Baker et al. |
| 5,693,310 A | 12/1997 | Gries et al. |
| 5,695,498 A | 12/1997 | Tower |
| 5,709,713 A | 1/1998 | Evans et al. |
| 5,713,953 A | 2/1998 | Vallana et al. |
| 5,716,370 A | 2/1998 | Williamson, IV et al. |
| 5,716,417 A | 2/1998 | Girard et al. |
| 5,720,391 A | 2/1998 | Dohm et al. |
| 5,728,068 A | 3/1998 | Leone et al. |
| 5,733,325 A | 3/1998 | Robinson et al. |
| 5,735,842 A | 4/1998 | Krueger et al. |
| 5,749,890 A | 5/1998 | Shaknovich |
| 5,756,476 A | 5/1998 | Epstein et al. |
| 5,769,812 A | 6/1998 | Stevens et al. |
| 5,800,456 A | 9/1998 | Maeda et al. |
| 5,800,531 A | 9/1998 | Cosgrove et al. |
| 5,807,405 A | 9/1998 | Vanney et al. |
| 5,817,126 A | 10/1998 | Imran |
| 5,824,041 A | 10/1998 | Lenker et al. |
| 5,824,043 A | 10/1998 | Cottone, Jr. |

| Patent | Kind | Date | Inventor |
|---|---|---|---|
| 5,824,053 | A | 10/1998 | Khosravi et al. |
| 5,824,055 | A | 10/1998 | Spiridigliozzi et al. |
| 5,824,056 | A | 10/1998 | Rosenberg |
| 5,824,064 | A | 10/1998 | Taheri |
| 5,840,081 | A | 11/1998 | Andersen et al. |
| 5,843,158 | A | 12/1998 | Lenker et al. |
| 5,855,597 | A | 1/1999 | Jayaraman |
| 5,855,601 | A | 1/1999 | Bessler et al. |
| 5,855,602 | A | 1/1999 | Angell |
| 5,860,966 | A | 1/1999 | Tower |
| 5,861,024 | A | 1/1999 | Rashidi |
| 5,861,028 | A | 1/1999 | Angell |
| 5,868,783 | A | 2/1999 | Tower |
| 5,876,448 | A | 3/1999 | Thompson et al. |
| 5,885,228 | A | 3/1999 | Rosenman et al. |
| 5,888,201 | A | 3/1999 | Stinson et al. |
| 5,891,191 | A | 4/1999 | Stinson |
| 5,895,399 | A | 4/1999 | Barbut et al. |
| 5,906,619 | A | 5/1999 | Olson et al. |
| 5,907,893 | A | 6/1999 | Zadno-Azizi et al. |
| 5,910,154 | A | 6/1999 | Tsugita et al. |
| 5,911,734 | A | 6/1999 | Tsugita et al. |
| 5,925,063 | A | 7/1999 | Khosravi |
| 5,944,738 | A | 8/1999 | Amplatz et al. |
| 5,954,766 | A | 9/1999 | Zadno-Azizi et al. |
| 5,957,949 | A | 9/1999 | Leonhardt et al. |
| 5,968,070 | A | 10/1999 | Bley et al. |
| 5,984,957 | A | 11/1999 | Laptewicz, Jr. et al. |
| 5,984,959 | A | 11/1999 | Robertson et al. |
| 5,993,469 | A | 11/1999 | McKenzie et al. |
| 5,997,557 | A | 12/1999 | Barbut et al. |
| 6,010,522 | A | 1/2000 | Barbut et al. |
| 6,022,370 | A | 2/2000 | Tower |
| 6,027,520 | A | 2/2000 | Tsugita et al. |
| 6,027,525 | A | 2/2000 | Suh et al. |
| 6,042,598 | A | 3/2000 | Tsugita et al. |
| 6,042,607 | A | 3/2000 | Williamson, IV et al. |
| 6,051,104 | A | 4/2000 | Oriaran et al. |
| 6,093,203 | A | 7/2000 | Uflacker |
| 6,123,723 | A | 9/2000 | Konya et al. |
| 6,132,473 | A | 10/2000 | Williams et al. |
| 6,142,987 | A | 11/2000 | Tsugita |
| 6,146,366 | A | 11/2000 | Schachar |
| 6,162,245 | A | 12/2000 | Jayaraman |
| 6,165,200 | A | 12/2000 | Tsugita et al. |
| 6,165,209 | A | 12/2000 | Patterson et al. |
| 6,168,579 | B1 | 1/2001 | Tsugita |
| 6,168,614 | B1 | 1/2001 | Andersen et al. |
| 6,171,327 | B1 | 1/2001 | Daniel et al. |
| 6,171,335 | B1 | 1/2001 | Wheatley et al. |
| 6,179,859 | B1 | 1/2001 | Bates |
| 6,187,016 | B1 | 2/2001 | Hedges et al. |
| 6,197,053 | B1 | 3/2001 | Cosgrove et al. |
| 6,200,336 | B1 | 3/2001 | Pavcnik et al. |
| 6,214,036 | B1 | 4/2001 | Letendre et al. |
| 6,221,006 | B1 | 4/2001 | Dubrul et al. |
| 6,221,091 | B1 | 4/2001 | Khosravi |
| 6,221,096 | B1 | 4/2001 | Aiba et al. |
| 6,221,100 | B1 | 4/2001 | Strecker |
| 6,231,544 | B1 | 5/2001 | Tsugita et al. |
| 6,231,551 | B1 | 5/2001 | Barbut |
| 6,241,757 | B1 | 6/2001 | An et al. |
| 6,245,102 | B1 | 6/2001 | Jayaraman |
| 6,258,114 | B1 | 7/2001 | Konya et al. |
| 6,258,115 | B1 | 7/2001 | Dubrul |
| 6,258,120 | B1 | 7/2001 | McKenzie et al. |
| 6,267,783 | B1 | 7/2001 | Letendre et al. |
| 6,270,513 | B1 | 8/2001 | Tsugita et al. |
| 6,277,555 | B1 | 8/2001 | Duran et al. |
| 6,299,637 | B1 | 10/2001 | Shaolian et al. |
| 6,302,906 | B1 | 10/2001 | Goicoechea et al. |
| 6,309,417 | B1 | 10/2001 | Spence et al. |
| 6,319,281 | B1 | 11/2001 | Patel |
| 6,327,772 | B1 | 12/2001 | Zadno-Azizi et al. |
| 6,336,934 | B1 | 1/2002 | Gilson et al. |
| 6,336,937 | B1 | 1/2002 | Vonesh et al. |
| 6,338,735 | B1 | 1/2002 | Stevens |
| 6,348,063 | B1 | 2/2002 | Yassour et al. |
| 6,352,708 | B1 | 3/2002 | Duran et al. |
| 6,361,545 | B1 | 3/2002 | Macoviak et al. |
| 6,371,970 | B1 | 4/2002 | Khosravi et al. |
| 6,371,983 | B1 | 4/2002 | Lane |
| 6,379,383 | B1 | 4/2002 | Palmaz et al. |
| 6,398,807 | B1 | 6/2002 | Chouinard et al. |
| 6,409,750 | B1 | 6/2002 | Hyodoh et al. |
| 6,416,510 | B1 | 7/2002 | Altman et al. |
| 6,425,916 | B1 | 7/2002 | Garrison et al. |
| 6,440,164 | B1 | 8/2002 | DiMatteo et al. |
| 6,454,799 | B1 | 9/2002 | Schreck |
| 6,458,153 | B1 | 10/2002 | Bailey et al. |
| 6,461,382 | B1 | 10/2002 | Cao |
| 6,468,303 | B1 | 10/2002 | Amplatz et al. |
| 6,468,660 | B2 | 10/2002 | Ogle et al. |
| 6,475,239 | B1 | 11/2002 | Campbell et al. |
| 6,482,228 | B1 | 11/2002 | Norred |
| 6,485,501 | B1 | 11/2002 | Green |
| 6,487,581 | B1 | 11/2002 | Spence et al. |
| 6,488,704 | B1 | 12/2002 | Connelly et al. |
| 6,494,909 | B2 | 12/2002 | Greenhalgh |
| 6,503,272 | B2 | 1/2003 | Duerig et al. |
| 6,508,833 | B2 | 1/2003 | Pavcnik |
| 6,527,800 | B1 | 3/2003 | McGuckin, Jr. et al. |
| 6,530,949 | B2 | 3/2003 | Konya et al. |
| 6,530,952 | B2 | 3/2003 | Vesely |
| 6,537,297 | B2 | 3/2003 | Tsugita et al. |
| 6,540,768 | B1 | 4/2003 | Diaz et al. |
| 6,562,058 | B2 | 5/2003 | Seguin et al. |
| 6,569,196 | B1 | 5/2003 | Vesely |
| 6,592,546 | B1 | 7/2003 | Barbut et al. |
| 6,592,614 | B2 | 7/2003 | Lenker et al. |
| 6,605,112 | B1 | 8/2003 | Moll et al. |
| 6,610,077 | B1 | 8/2003 | Hancock et al. |
| 6,616,682 | B2 | 9/2003 | Joergensen et al. |
| 6,622,604 | B1 | 9/2003 | Chouinard et al. |
| 6,623,518 | B2 | 9/2003 | Thompson et al. |
| 6,632,243 | B1 | 10/2003 | Zadno-Azizi et al. |
| 6,635,068 | B1 | 10/2003 | Dubrul et al. |
| 6,635,079 | B2 | 10/2003 | Unsworth et al. |
| 6,652,571 | B1 | 11/2003 | White et al. |
| 6,652,578 | B2 | 11/2003 | Bailey et al. |
| 6,663,588 | B2 | 12/2003 | DuBois et al. |
| 6,663,663 | B2 | 12/2003 | Kim et al. |
| 6,669,724 | B2 | 12/2003 | Park et al. |
| 6,673,089 | B1 | 1/2004 | Yassour et al. |
| 6,673,109 | B2 | 1/2004 | Cox |
| 6,676,692 | B2 | 1/2004 | Rabkin et al. |
| 6,676,698 | B2 | 1/2004 | McGuckin, Jr. et al. |
| 6,682,543 | B2 | 1/2004 | Barbut et al. |
| 6,682,558 | B2 | 1/2004 | Tu et al. |
| 6,682,559 | B2 | 1/2004 | Myers et al. |
| 6,685,739 | B2 | 2/2004 | DiMatteo et al. |
| 6,689,144 | B2 | 2/2004 | Gerberding |
| 6,689,164 | B1 | 2/2004 | Seguin |
| 6,692,512 | B2 | 2/2004 | Jang |
| 6,695,864 | B2 | 2/2004 | Macoviak et al. |
| 6,695,865 | B2 | 2/2004 | Boyle et al. |
| 6,702,851 | B1 | 3/2004 | Chinn et al. |
| 6,712,842 | B1 | 3/2004 | Gifford et al. |
| 6,712,843 | B2 | 3/2004 | Elliott |
| 6,714,842 | B1 | 3/2004 | Ito |
| 6,719,789 | B2 | 4/2004 | Cox |
| 6,723,116 | B2 | 4/2004 | Taheri |
| 6,730,118 | B2 | 5/2004 | Spenser et al. |
| 6,730,377 | B2 | 5/2004 | Wang |
| 6,733,525 | B2 | 5/2004 | Yang et al. |
| 6,736,846 | B2 | 5/2004 | Cox |
| 6,752,828 | B2 | 6/2004 | Thornton |
| 6,758,855 | B2 | 7/2004 | Fulton, III et al. |
| 6,764,503 | B1 | 7/2004 | Ishimaru |
| 6,764,509 | B2 | 7/2004 | Chinn et al. |
| 6,767,345 | B2 | 7/2004 | St. Germain et al. |
| 6,769,434 | B2 | 8/2004 | Liddicoat et al. |
| 6,773,454 | B2 | 8/2004 | Wholey et al. |
| 6,776,791 | B1 | 8/2004 | Stallings et al. |
| 6,786,925 | B1 | 9/2004 | Schoon et al. |
| 6,790,229 | B1 | 9/2004 | Berreklouw |
| 6,790,230 | B2 | 9/2004 | Beyersdorf et al. |
| 6,790,237 | B2 | 9/2004 | Stinson |

| | | | | | | |
|---|---|---|---|---|---|---|
| 6,792,979 B2 | 9/2004 | Hyodoh et al. | 2001/0041930 A1* | 11/2001 | Globerman et al. | 623/1.16 |
| 6,797,002 B2 | 9/2004 | Spence et al. | 2001/0044634 A1 | 11/2001 | Don Michael et al. | |
| 6,814,746 B2 | 11/2004 | Thompson et al. | 2001/0044652 A1 | 11/2001 | Moore | |
| 6,821,297 B2 | 11/2004 | Snyders | 2001/0044656 A1 | 11/2001 | Williamson et al. | |
| 6,830,585 B1 | 12/2004 | Artof et al. | 2002/0002396 A1 | 1/2002 | Fulkerson | |
| 6,837,901 B2 | 1/2005 | Rabkin et al. | 2002/0010489 A1 | 1/2002 | Grayzel et al. | |
| 6,840,957 B2 | 1/2005 | DiMatteo et al. | 2002/0026233 A1 | 2/2002 | Shaknovich | |
| 6,843,802 B1 | 1/2005 | Villalobos et al. | 2002/0029981 A1 | 3/2002 | Nigam | |
| 6,849,085 B2 | 2/2005 | Marton | 2002/0032480 A1 | 3/2002 | Spence et al. | |
| 6,863,668 B2 | 3/2005 | Gillespie et al. | 2002/0032481 A1* | 3/2002 | Gabbay | 623/2.11 |
| 6,866,650 B2 | 3/2005 | Stevens et al. | 2002/0055769 A1* | 5/2002 | Wang | 623/1.13 |
| 6,872,223 B2 | 3/2005 | Roberts et al. | 2002/0058995 A1 | 5/2002 | Stevens | |
| 6,872,226 B2 | 3/2005 | Cali et al. | 2002/0077696 A1 | 6/2002 | Zadno-Azizi et al. | |
| 6,875,231 B2 | 4/2005 | Anduiza et al. | 2002/0082609 A1 | 6/2002 | Green | |
| 6,881,220 B2 | 4/2005 | Edwin et al. | 2002/0095173 A1 | 7/2002 | Mazzocchi et al. | |
| 6,887,266 B2 | 5/2005 | Williams et al. | 2002/0095209 A1 | 7/2002 | Zadno-Azizi et al. | |
| 6,890,340 B2 | 5/2005 | Duane | 2002/0111674 A1 | 8/2002 | Chouinard et al. | |
| 6,893,459 B1 | 5/2005 | Macoviak | 2002/0120328 A1 | 8/2002 | Pathak et al. | |
| 6,893,460 B2 | 5/2005 | Spenser et al. | 2002/0138138 A1* | 9/2002 | Yang | 623/2.18 |
| 6,905,743 B1 | 6/2005 | Chen et al. | 2002/0151970 A1 | 10/2002 | Garrison et al. | |
| 6,908,481 B2 | 6/2005 | Cribier | 2002/0161392 A1 | 10/2002 | Dubrul | |
| 6,911,036 B2 | 6/2005 | Douk et al. | 2002/0161394 A1 | 10/2002 | Macoviak et al. | |
| 6,911,043 B2 | 6/2005 | Myers et al. | 2002/0177766 A1 | 11/2002 | Mogul | |
| 6,936,058 B2 | 8/2005 | Forde et al. | 2002/0188341 A1 | 12/2002 | Elliott | |
| 6,936,067 B2 | 8/2005 | Buchanan | 2002/0188344 A1 | 12/2002 | Bolea et al. | |
| 6,951,571 B1 | 10/2005 | Srivastava | 2003/0023303 A1* | 1/2003 | Palmaz et al. | 623/2.18 |
| 6,953,332 B1 | 10/2005 | Kurk et al. | 2003/0036791 A1* | 2/2003 | Philipp et al. | 623/1.11 |
| 6,964,673 B2 | 11/2005 | Tsugita et al. | 2003/0040771 A1 | 2/2003 | Hyodoh et al. | |
| 6,969,395 B2 | 11/2005 | Eskuri et al. | 2003/0040772 A1 | 2/2003 | Hyodoh et al. | |
| 6,972,025 B2 | 12/2005 | WasDyke | 2003/0050694 A1 | 3/2003 | Yang et al. | |
| 6,974,464 B2 | 12/2005 | Quijano et al. | 2003/0055495 A1 | 3/2003 | Pease et al. | |
| 6,974,474 B2 | 12/2005 | Pavcnik et al. | 2003/0060844 A1 | 3/2003 | Borillo et al. | |
| 6,974,476 B2 | 12/2005 | McGuckin, Jr. et al. | 2003/0070944 A1 | 4/2003 | Nigam | |
| 6,979,350 B2 | 12/2005 | Moll et al. | 2003/0109924 A1 | 6/2003 | Cribier | |
| 6,984,242 B2 | 1/2006 | Campbell et al. | 2003/0109930 A1 | 6/2003 | Bluni et al. | |
| 6,989,027 B2 | 1/2006 | Allen et al. | 2003/0125795 A1 | 7/2003 | Pavcnik et al. | |
| 7,011,681 B2 | 3/2006 | Vesely | 2003/0130729 A1 | 7/2003 | Paniagua et al. | |
| 7,018,406 B2 | 3/2006 | Seguin et al. | 2003/0144732 A1 | 7/2003 | Cosgrove et al. | |
| 7,025,791 B2 | 4/2006 | Levine et al. | 2003/0149476 A1 | 8/2003 | Damm et al. | |
| 7,037,331 B2 | 5/2006 | Mitelberg et al. | 2003/0149478 A1 | 8/2003 | Figulla et al. | |
| 7,041,132 B2 | 5/2006 | Quijano et al. | 2003/0176884 A1 | 9/2003 | Berrada et al. | |
| 7,097,658 B2 | 8/2006 | Oktay | 2003/0181850 A1 | 9/2003 | Diamond et al. | |
| 7,122,020 B2 | 10/2006 | Mogul | 2003/0187495 A1 | 10/2003 | Cully et al. | |
| 7,125,418 B2 | 10/2006 | Duran et al. | 2003/0199913 A1 | 10/2003 | Dubrul et al. | |
| 7,166,097 B2 | 1/2007 | Barbut | 2003/0199971 A1 | 10/2003 | Tower et al. | |
| 7,175,653 B2 | 2/2007 | Gaber | 2003/0199972 A1 | 10/2003 | Zadno-Azizi et al. | |
| 7,175,654 B2 | 2/2007 | Bonsignore et al. | 2003/0208224 A1 | 11/2003 | Broome | |
| 7,175,656 B2 | 2/2007 | Khairkhahan | 2003/0212429 A1 | 11/2003 | Keegan et al. | |
| 7,189,258 B2 | 3/2007 | Johnson et al. | 2003/0212452 A1 | 11/2003 | Zadno-Azizi et al. | |
| 7,191,018 B2 | 3/2007 | Gielen et al. | 2003/0212454 A1 | 11/2003 | Scott et al. | |
| 7,201,772 B2* | 4/2007 | Schwammenthal et al. . 623/1.26 | 2003/0216774 A1 | 11/2003 | Larson | |
| 7,235,093 B2 | 6/2007 | Gregorich | 2003/0229390 A1 | 12/2003 | Ashton et al. | |
| 7,258,696 B2 | 8/2007 | Rabkin et al. | 2003/0233117 A1 | 12/2003 | Adams et al. | |
| 7,267,686 B2 | 9/2007 | DiMatteo et al. | 2004/0034411 A1 | 2/2004 | Quijano et al. | |
| 7,276,078 B2 | 10/2007 | Spenser et al. | 2004/0039436 A1 | 2/2004 | Spenser et al. | |
| 7,322,932 B2 | 1/2008 | Xie et al. | 2004/0049224 A1 | 3/2004 | Buehlmann et al. | |
| 7,329,279 B2 | 2/2008 | Haug et al. | 2004/0049226 A1 | 3/2004 | Keegan et al. | |
| 7,374,560 B2 | 5/2008 | Ressemann et al. | 2004/0049262 A1 | 3/2004 | Obermiller et al. | |
| 7,381,219 B2 | 6/2008 | Salahieh et al. | 2004/0059409 A1* | 3/2004 | Stenzel | 623/1.15 |
| 7,381,220 B2 | 6/2008 | Macoviak et al. | 2004/0073198 A1 | 4/2004 | Gilson et al. | |
| 7,399,315 B2* | 7/2008 | Iobbi | 623/1.26 | 2004/0082904 A1 | 4/2004 | Houde et al. | |
| 7,445,631 B2 | 11/2008 | Salahieh et al. | 2004/0082967 A1 | 4/2004 | Broome et al. | |
| 7,470,285 B2 | 12/2008 | Nugent et al. | 2004/0088045 A1 | 5/2004 | Cox | |
| 7,510,574 B2 | 3/2009 | Le et al. | 2004/0093016 A1 | 5/2004 | Root et al. | |
| 7,524,330 B2 | 4/2009 | Berreklouw | 2004/0097788 A1 | 5/2004 | Mourlas et al. | |
| 7,530,995 B2 | 5/2009 | Quijano et al. | 2004/0098022 A1 | 5/2004 | Barone | |
| 7,544,206 B2 | 6/2009 | Cohn | 2004/0098099 A1* | 5/2004 | McCullagh et al. | 623/1.15 |
| 7,622,276 B2 | 11/2009 | Cunanan et al. | 2004/0111096 A1 | 6/2004 | Tu et al. | |
| 7,628,803 B2 | 12/2009 | Pavcnik et al. | 2004/0116951 A1 | 6/2004 | Rosengart | |
| 7,632,298 B2 | 12/2009 | Hijlkema et al. | 2004/0117004 A1 | 6/2004 | Osborne et al. | |
| 7,722,666 B2 | 5/2010 | Lafontaine | 2004/0117009 A1 | 6/2004 | Cali et al. | |
| 7,748,389 B2 | 7/2010 | Salahieh et al. | 2004/0122468 A1 | 6/2004 | Yodfat et al. | |
| 7,780,725 B2 | 8/2010 | Haug et al. | 2004/0122516 A1 | 6/2004 | Fogarty et al. | |
| 7,803,185 B2 | 9/2010 | Gabbay | 2004/0127979 A1 | 7/2004 | Wilson et al. | |
| 7,833,262 B2 | 11/2010 | McGuckin, Jr. et al. | 2004/0133274 A1 | 7/2004 | Webler et al. | |
| 7,846,204 B2 | 12/2010 | Letac et al. | 2004/0138694 A1 | 7/2004 | Tran et al. | |
| 2001/0007956 A1 | 7/2001 | Letac et al. | 2004/0138742 A1 | 7/2004 | Myers et al. | |
| 2001/0039450 A1 | 11/2001 | Pavcnik et al. | 2004/0148021 A1 | 7/2004 | Cartledge et al. | |
| 2001/0041928 A1 | 11/2001 | Pavcnik et al. | 2004/0153094 A1 | 8/2004 | Dunfee et al. | |

| | | |
|---|---|---|
| 2004/0158277 A1 | 8/2004 | Lowe et al. |
| 2004/0167565 A1 | 8/2004 | Beulke et al. |
| 2004/0181140 A1 | 9/2004 | Falwell et al. |
| 2004/0186563 A1 | 9/2004 | Lobbi |
| 2004/0204755 A1 | 10/2004 | Robin |
| 2004/0210304 A1 | 10/2004 | Seguin et al. |
| 2004/0215331 A1 | 10/2004 | Chew et al. |
| 2004/0215339 A1 | 10/2004 | Drasler et al. |
| 2004/0220655 A1 | 11/2004 | Swanson et al. |
| 2004/0225321 A1 | 11/2004 | Krolik et al. |
| 2004/0225355 A1 | 11/2004 | Stevens |
| 2004/0243221 A1 | 12/2004 | Fawzi et al. |
| 2004/0254636 A1 | 12/2004 | Flagle et al. |
| 2004/0260390 A1 | 12/2004 | Sarac et al. |
| 2005/0033398 A1 | 2/2005 | Seguin |
| 2005/0033402 A1 | 2/2005 | Cully et al. |
| 2005/0043711 A1 | 2/2005 | Corcoran et al. |
| 2005/0043757 A1 | 2/2005 | Arad et al. |
| 2005/0043790 A1 | 2/2005 | Seguin |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0075584 A1 | 4/2005 | Cali |
| 2005/0075662 A1 | 4/2005 | Pedersen et al. |
| 2005/0075712 A1 | 4/2005 | Biancucci et al. |
| 2005/0075717 A1 | 4/2005 | Nguyen et al. |
| 2005/0075719 A1 | 4/2005 | Bergheim |
| 2005/0075724 A1 | 4/2005 | Svanidze et al. |
| 2005/0075730 A1 | 4/2005 | Myers et al. |
| 2005/0075731 A1 | 4/2005 | Artof et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | WasDyke |
| 2005/0113910 A1 | 5/2005 | Paniagua et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143807 A1 | 6/2005 | Pavcnik et al. |
| 2005/0143809 A1 | 6/2005 | Salahieh et al. |
| 2005/0165352 A1 | 7/2005 | Henry et al. |
| 2005/0165477 A1 | 7/2005 | Anduiza et al. |
| 2005/0165479 A1 | 7/2005 | Drews et al. |
| 2005/0182486 A1 | 8/2005 | Gabbay |
| 2005/0197694 A1 | 9/2005 | Pai et al. |
| 2005/0197695 A1* | 9/2005 | Stacchino et al. ............ 623/2.18 |
| 2005/0203549 A1 | 9/2005 | Realyvasquez |
| 2005/0203614 A1 | 9/2005 | Forster |
| 2005/0203615 A1 | 9/2005 | Forster |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0209580 A1 | 9/2005 | Freyman |
| 2005/0228472 A1 | 10/2005 | Case et al. |
| 2005/0228495 A1 | 10/2005 | Macoviak |
| 2005/0240200 A1 | 10/2005 | Bergheim |
| 2005/0240262 A1 | 10/2005 | White |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283231 A1 | 12/2005 | Haug et al. |
| 2005/0283962 A1 | 12/2005 | Boudjemline |
| 2006/0004439 A1 | 1/2006 | Spenser et al. |
| 2006/0004442 A1* | 1/2006 | Spenser et al. ............... 623/2.11 |
| 2006/0015168 A1 | 1/2006 | Gunderson |
| 2006/0058872 A1 | 3/2006 | Salahieh et al. |
| 2006/0155312 A1 | 7/2006 | Levine et al. |
| 2006/0161249 A1 | 7/2006 | Realyvasquez et al. |
| 2006/0173524 A1 | 8/2006 | Salahieh et al. |
| 2006/0195183 A1* | 8/2006 | Navia et al. ................. 623/2.18 |
| 2006/0259134 A1 | 11/2006 | Schwammenthal et al. |
| 2006/0271166 A1 | 11/2006 | Thill et al. |
| 2006/0287668 A1 | 12/2006 | Fawzi et al. |
| 2007/0010876 A1 | 1/2007 | Salahieh et al. |
| 2007/0010877 A1 | 1/2007 | Salahieh et al. |
| 2007/0016286 A1 | 1/2007 | Herrmann et al. |
| 2007/0055340 A1 | 3/2007 | Pryor |
| 2007/0061008 A1 | 3/2007 | Salahieh et al. |
| 2007/0112355 A1 | 5/2007 | Salahieh et al. |
| 2007/0118214 A1 | 5/2007 | Salahieh et al. |
| 2007/0162107 A1 | 7/2007 | Haug et al. |
| 2007/0173918 A1 | 7/2007 | Dreher et al. |
| 2007/0203503 A1 | 8/2007 | Salahieh et al. |
| 2007/0244552 A1 | 10/2007 | Salahieh et al. |
| 2007/0288089 A1 | 12/2007 | Gurskis et al. |
| 2008/0009940 A1 | 1/2008 | Cribier |
| 2008/0082165 A1 | 4/2008 | Wilson et al. |
| 2008/0125859 A1 | 5/2008 | Salahieh et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0269878 A1 | 10/2008 | Iobbi |
| 2008/0288054 A1 | 11/2008 | Pulnev et al. |
| 2009/0005863 A1 | 1/2009 | Goetz et al. |
| 2009/0030512 A1 | 1/2009 | Thielen et al. |
| 2009/0054969 A1 | 2/2009 | Salahieh et al. |
| 2009/0076598 A1 | 3/2009 | Salahieh et al. |
| 2009/0171456 A1 | 7/2009 | Kveen et al. |
| 2009/0222076 A1 | 9/2009 | Figulla et al. |
| 2009/0264997 A1 | 10/2009 | Salahieh et al. |
| 2009/0299462 A1 | 12/2009 | Fawzi et al. |
| 2010/0049313 A1 | 2/2010 | Alon et al. |
| 2010/0121434 A1 | 5/2010 | Paul et al. |
| 2010/0219092 A1 | 9/2010 | Salahieh et al. |
| 2010/0280495 A1 | 11/2010 | Paul et al. |

FOREIGN PATENT DOCUMENTS

| | | |
|---|---|---|
| CN | 1338951 A | 3/2002 |
| DE | 19532846 | 3/1997 |
| DE | 19546692 | 6/1997 |
| DE | 19857887 | 7/2000 |
| DE | 19907646 | 8/2000 |
| DE | 10049812 | 4/2002 |
| DE | 10049813 | 4/2002 |
| DE | 10049814 | 4/2002 |
| DE | 10049815 | 10/2005 |
| EP | 0103546 | 5/1988 |
| EP | 0144167 | 11/1989 |
| EP | 0409929 | 4/1997 |
| EP | 0409929 B1 | 4/1997 |
| EP | 1000590 | 5/2000 |
| EP | 1057459 | 12/2000 |
| EP | 1057460 | 12/2000 |
| EP | 1088529 | 4/2001 |
| EP | 0937439 | 9/2003 |
| EP | 1340473 | 9/2003 |
| EP | 1356793 | 10/2003 |
| EP | 1042045 | 5/2004 |
| EP | 0819013 | 6/2004 |
| EP | 1435879 | 7/2004 |
| EP | 1439800 | 7/2004 |
| EP | 1589902 | 8/2004 |
| EP | 1605871 | 9/2004 |
| EP | 1229864 | 4/2005 |

| | | |
|---|---|---|
| EP | 1430853 | 6/2005 |
| EP | 1059894 | 7/2005 |
| EP | 1551274 | 7/2005 |
| EP | 1551336 | 7/2005 |
| EP | 1078610 | 8/2005 |
| EP | 1562515 | 8/2005 |
| EP | 1576937 A2 | 9/2005 |
| EP | 1582178 A2 | 10/2005 |
| EP | 1582179 A2 | 10/2005 |
| EP | 1469797 | 11/2005 |
| EP | 1600121 A1 | 11/2005 |
| EP | 1156757 B1 | 12/2005 |
| EP | 1616531 | 1/2006 |
| SU | 1271508 | 11/1986 |
| SU | 1371700 | 2/1988 |
| WO | 9117720 | 11/1991 |
| WO | 9217118 | 10/1992 |
| WO | WO 93/15693 | 8/1993 |
| WO | WO 95/04556 | 2/1995 |
| WO | WO 95/29640 | 11/1995 |
| WO | WO 96/14032 | 5/1996 |
| WO | WO 96/24306 A1 | 8/1996 |
| WO | WO 98/36790 | 8/1998 |
| WO | WO 98/50103 | 11/1998 |
| WO | WO 98/57599 A2 | 12/1998 |
| WO | 9933414 | 7/1999 |
| WO | 9940964 | 8/1999 |
| WO | 9947075 | 9/1999 |
| WO | WO 99/44542 | 9/1999 |
| WO | WO 00/09059 | 2/2000 |
| WO | 0041652 | 7/2000 |
| WO | 0044211 | 7/2000 |
| WO | 0044311 | 8/2000 |
| WO | WO 00/44308 | 8/2000 |
| WO | WO 00/44313 | 8/2000 |
| WO | WO 00/49970 | 8/2000 |
| WO | WO 00/67661 | 11/2000 |
| WO | WO 01/05331 | 1/2001 |
| WO | WO 01/08596 | 2/2001 |
| WO | WO 01/10320 | 2/2001 |
| WO | WO 01/10343 | 2/2001 |
| WO | WO 01/35870 | 5/2001 |
| WO | 0154625 | 8/2001 |
| WO | WO 01/64137 | 9/2001 |
| WO | 0197715 | 12/2001 |
| WO | 0241789 | 5/2002 |
| WO | WO 02/36048 | 5/2002 |
| WO | WO 02/41789 A2 | 5/2002 |
| WO | 0243620 | 6/2002 |
| WO | 0247575 | 6/2002 |
| WO | WO 02/100297 | 12/2002 |
| WO | WO 03/003943 | 1/2003 |
| WO | WO 03/003949 | 1/2003 |
| WO | WO 03/011195 | 2/2003 |
| WO | 03094793 | 11/2003 |
| WO | 03094797 | 11/2003 |
| WO | WO 03/015851 | 11/2003 |
| WO | WO 2004/019811 | 3/2004 |
| WO | WO 2004/023980 | 3/2004 |
| WO | WO 2004/041126 | 5/2004 |
| WO | WO 2004/047681 | 6/2004 |
| WO | 2004082536 | 9/2004 |
| WO | 2004089250 | 10/2004 |
| WO | 2004089253 | 10/2004 |
| WO | 2004105651 | 12/2004 |
| WO | 2005002466 | 1/2005 |
| WO | 2005004753 | 1/2005 |
| WO | 2005009285 | 2/2005 |
| WO | 2005011534 | 2/2005 |
| WO | 2005011535 | 2/2005 |
| WO | 2005023155 | 3/2005 |
| WO | 2005027790 | 3/2005 |
| WO | 2005046528 | 5/2005 |
| WO | 2005048883 | 6/2005 |
| WO | WO 2005/084595 | 9/2005 |
| WO | WO 2005/087140 A1 | 9/2005 |
| WO | 2005096993 | 10/2005 |
| WO | 2007044285 | 4/2007 |

OTHER PUBLICATIONS

Salahieh, et al., U.S. Appl. No. 11/532,019, "Methods and apparatus for endovascularly replacing heart valve," filed Sep. 14, 2006.

Haug, et al; U.S. Appl. No. 11/716,123, entitled "Methods and apparatus for endovascularly replacing a heart valve," filed Mar. 9, 2007.

Salahieh, et al; U.S. Appl. No. 11/706,549, entitled "Systems and Methods for Delivering a Medical Implant," filed Feb. 14, 2007.

Salahieh, et al; U.S. Appl. No. 11/732,906 entitled "Assessing the location and performance of replacement heart valves," filed Apr. 4, 2007.

Fawzi, et al., U.S. Appl. No. 11/155,309, entitled "Apparatus and methods for intravascular embolic protection," filed Jun. 16, 2005.

Salahieh, et al., U.S. Appl. No. 11/232,441, entitled "Methods and apparatus for endovascular heart valve replacement comprising tissue grasping elements," filed Sep. 20, 2005.

Salahieh, et al., U.S. Appl. No. 11/274,889, entitled "Medical implant deployment tool," filed Nov. 14, 2005.

Salahieh, et al., U.S. Appl. No. 11/314,183, entitled "Medical Device Delivery," filed Dec. 20, 2005.

Salahieh, et al., U.S. Appl. No. 11/314,969, entitled "Methods and Apparatus for Performing Valvuloplasty," filed Dec. 20, 2005.

Salahieh, et al., U.S. Appl. No. 12/264,082 entitled "Repositionable heart valve and method," filed Nov. 3, 2008.

Salahieh, et al., U.S. Appl. No. 12/269,213 entitled "Everting heart valve," filed Nov. 12, 2008.

Salahieh, et al., U.S. Appl. No. 12/132,304 entitled "Low profile heart valve and delivery system," filed Jun. 3, 2008.

Haug et al.; U.S. Appl. No. 12/492,512 entitled "Everting Heart Valve," filed Jun. 26, 2009.

Haug et al.; U.S. Appl. No. 12/028,452 entitled "Methods and apparatus for endovascularly replacing a patient's heart valve," filed Feb. 8, 2008.

Salahieh, et al, U.S. Appl. No. 11/275,912, entitled "Medical Implant Delivery and Deployment Tool," filed Feb. 2, 2006.

Salahieh, et al., U.S. Appl. No. 11/275,913, entitled "Two-Part Package for Medical Implant," filed Feb. 2, 2006.

Paul et al.; U.S. Appl. No. 12/578,463 entitled "Medical Devices and Delivery Systems for Delivering Medical Devices," filed Oct. 13, 2009.

Paul et al.; U.S. Appl. No. 12/578,447 entitled "Medical Devices and Delivery Systems for Delivering Medical Devices," filed Oct. 13, 2009.

Andersen, H.R. et al., "Transluminal implantation of artificial heart valves. Description of a new expandable aortic valve and initial results with implantation by catheter technique in closed chest pigs." *Euro. Heart J.* (1992) 13:704-708.

Atwood, A. et al., "Insertion of Heart Valves by Catheterization." Project Supervised by Prof Y. Muftu of Northeaster University (2001-2002): 36-40.

Bodnar, E. et al., Replacement Cardiac Valves, Pergamon Publishing Corporation, New York, (1991): 307-322.

Boudjemline, Y. et al., "Percutaneious implantation of a biological valve in the aorta to treat aortic valve insufficiency—a sheep study." *Med Sci.Monit.* (2002) vol. 8, No. 4: BR113-116.

Boudjemline, Y. et al., "Percutaneous implantation of a valve in the descending aorta in lambs." *Euro. Heart J.* (2002) 23(13): 1045-1049.

Boudjemline, Y. et al., "Percutaneous pulmonary valve replacement in a large right ventricular outflow tract: an experimental study." *Journal of the Americal College of Cardiology.* (2004), vol. 43, No. 6: 1082-1087.

Boudjemline, Y. et al., "Percutaneous valve insertion: A new approach?" *J. of Thoracic and Cardio. Surg.* (2003) 125(3): 741-743.

Boudjemline, Y. et al., "Steps Toward Percutaneous Aortic Valve Replacement." *Circulation.* (2002): 775-778.

Cribier, A. et al., "Early Experience with Percutaneous Transcatheter Implantation of Heart Valve Prosthesis for the Treatment of End-Stage Inoperable Patients with Calcific Aortic Stenosis." *J. or Am. Coll. of Cardio.* (2004) 43(4): 698-703.

Cribier, A., et al., "Percutaneous Transcatheter Implantation of an Aortic Valve Prosthesis for Calcific Aortic Stenosis: First Human Case Description." *Circulation.* (2002): 3006-3008.

Cribier, A., et al., "Percutaneous Transcatheter Implantation of an Aortic Valve Prosthesis for Calcific Aortic Stenosis: First Human Case." Percutaneous Valve Technologies, Inc. (2002).

Ferrari, M. et al., "Percutaneous transvascular aortic valve replacement with self expanding stent-valve device." Poster from the presentation given at SMIT 2000, 12th International Conference (Sep. 5, 2000).

Hijazi, Z.M., "Transcatheter Valve Replacement: A New Era of Percutaneous Cardiac Intervention Begins." *J. of Am. College of Cardio.* (2004) 43(6): 1088-1089.

Huber, C.H. et al., "Do valved stents compromise coronary flow?" *European Jouranl of Cardio-thoracic Surgery.* (2004), vol. 25: 754-759.

Knudsen, L. L. et al., "Catheter-implanted prosthetic heart valves." *Int'l J. of Art. Organs.* (1993) 16(5): 253-263.

Kort, S. et al., "Minimally invasive aortic valve replacement: Echocardiographic and clinical results." *Am. Heart J.* (2001) 142(3): 476-481.

Love, C. et al., "The Autogenous Tissue Heart Valve: Current Status." *Journal of Caridac Surgery.* (1991) 6(4): 499-507.

Lutter, G. et al., "Percutaneous aortic valve replacement: An experimental study. I. Studies on implantation." *J. of Thoracic and Cardio. Surg.* (2002) 123(4): 768-776.

Moulopoulos, S. D. et al., "Catheter-Mounted Aortic Valves." *Annals of Thoracic Surg.* (1971) 11(5): 423-430.

Paniagua, D. et al., "Percutaneous heart valve in the chronic in vitro testing model." *Circulation.* (2002), 106:e51-e52, American heart Association, Inc.

Paniagua, D. et al., Heart Watch (2004), Spring, 2004 Edition, Texas Heart Institute.

Pavcnik, D. et al., "Percutaneous bioprosthetic venous valve: A long-term study in sheep." *J. of Vascular Surg.* (2002) 35(3): 598-603.

Phillips, S. J. at al., "A Temporary Catheter-Tip Aortic Valve: Hemodynamic Effects on Experimental Acute Aortic Insufficiency." *Annals of Thoracic Surg.* (1976) 21(2): 134-136.

Sochman, J. et al., "Percutaneous Transcatheter Aortic Disc Valve Prosthesis Implantation: A Feasibility Study." *Cardiovasc. Intervent. Radiol.* (2000) 23: 384-388.

Stuart, M., "In Heart Valves, A Brave, New Non-Surgical World." *Start-Up* (2004): 9-17.

Vahanian, A. et al., "Percutaneous Approaches to Valvular Disease." *Circulation.* (2004) 109: 1572-1579.

Van Herwerden, L. A. et al., "Percutaneous valve implantation: back to the future?" *Euro. Heart J.* (2002) 23(18): 1415-1416.

Zhou, J. Q. et al., "Self-expandable valved stent of large size: off-bypass implantation in pulmonary position." *Eur. J. Cardiothorac Surg.* (2003) 24, 212-216.

A Matter of Size, Treiennial Review of the National Nanotechnology Initiative, 2006, v-13, The National Academies Press, Washington, DC htt://www. Nap.edu/cataog/11752.html.

Civil Code, Section 3426-3426.11.

Cunanan, Crystal, M., M.S., et al., Tissue Characterization and Calcification Potential of Commerical Bioprosthetic Heart Valves, 2001, S417-21, Elsevier Science Inc.

Hourihan, Maribeth, et al., Transcatheter Umbrella Closure of Valvular and Paravalvular Leaks, Nov. 15, 1992, 1371-7, vol. 20, No. 6, JACC, Boston Massachusetts.

J.C. Laborde, Percutaneous implantation of the corevalve aortic valve prosthesis for patients presenting high risk for surgical valve replacement, 2006, 472-474, EuroIntervention.

H.R. Cunliffe, et al., Glutaraldehyde Inactivation of Exotic Animal Viruses in Swine Heart Tissue, May 1979, 1044-1046, vol. 37, No. 5., Applied and Environmental Microbiology, Greenport, New York.

Heart Valve Materials—Bovine (cow), Equine & Porcine Pericardium, Maverick Biosciences PTY. LTD, Jan. 7, 2011, http://www.maverickbio.com/biological-medical-device-materials.php?htm.

Levy, Charles, M.D., Mycobacterium Chelonei Infection of Porcine Heart Valves, Sep. 22, 1977, vol. 297, No. 12, The New England Journal of Medicine, Washington, D.C.

LinkedIn, Ken Michlitsch, Jan. 7, 2010, http://www.linkedin.com/pug/ken-michlitsc/7/7b/920.

M.N. Helmus, Mechanical and bioprosthetic heart valves in biomaterials for artificial organs, 114-162, Woodhead Publishing. Southern Lights Biomaterials Homepage.

Pavcnik, D. et al., "Percutaneous bioprosthetic venous valve: A long term study in sheep". J. of Vascular Surg. (2002) 35:3, 598-603.

Topol, Eric J., M.D., Percutaneous Expandable Prosthetic Valves, Textbook of Interventional Cardiology, 1994, 1268-1276, vol. 2, W.B. Saunders Company, Philadelphia.

Pericardial Heart Valves, Edwards Lifesciences, Cardiovascular Surgery FAQ, Nov. 14, 2010, http://www.edwards.com/products/cardiovascularsurgeryfaq.htm.

VentureBeatProfiles, Claudio Argento, Jan. 7, 2010, http://venturebeatprofiles.com/person/profile/claudio-argento.

Stassano, Paolo, Mid-term results of the valve-on-valve technique for bioprosthetic failure, 2000, 453-457, European Journal of Cardio-thoracic Surgery.

\* cited by examiner

FIG IB

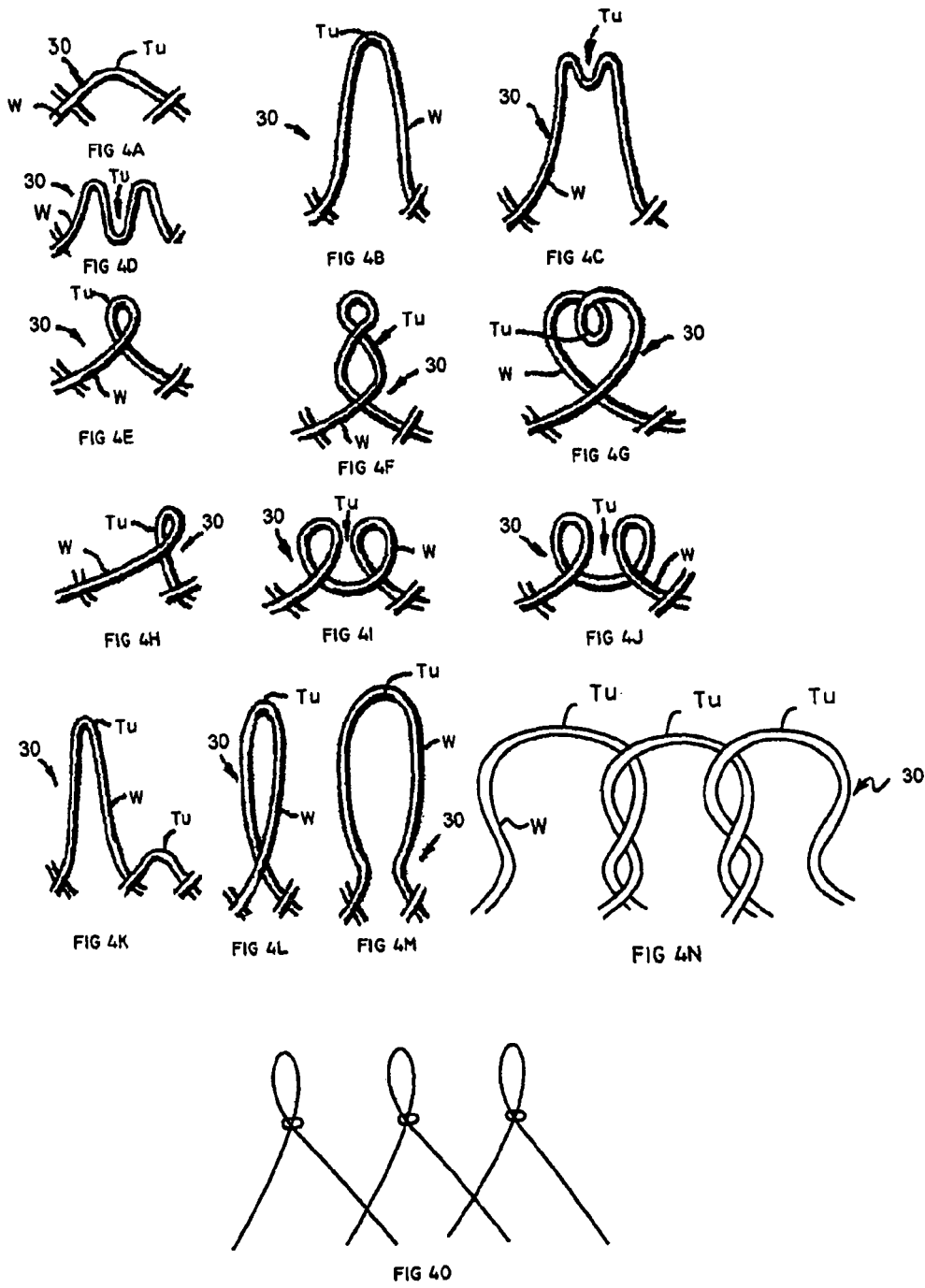

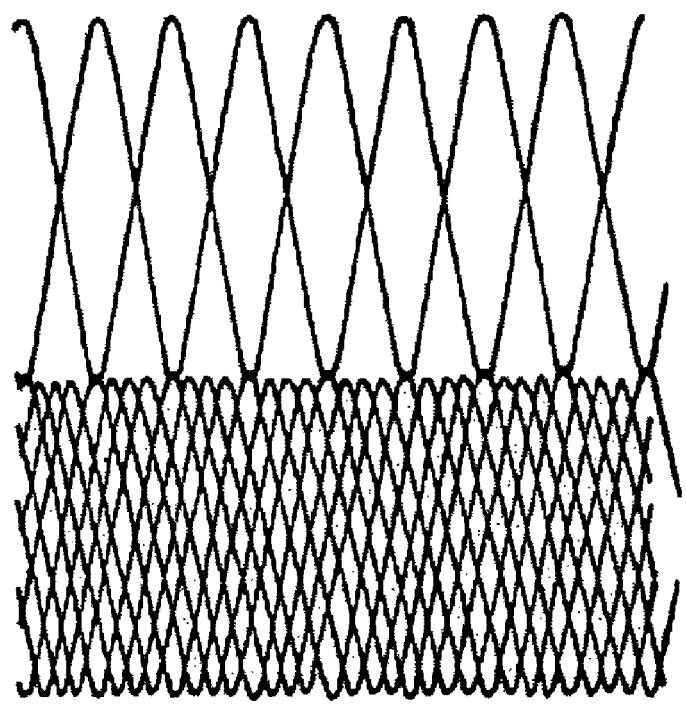
FIG IIA

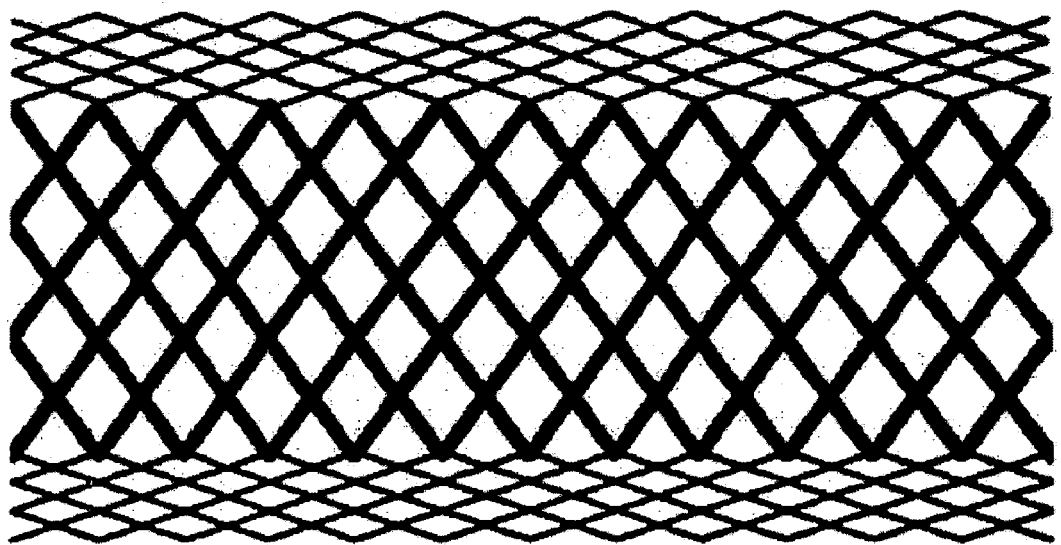
FIG IIB

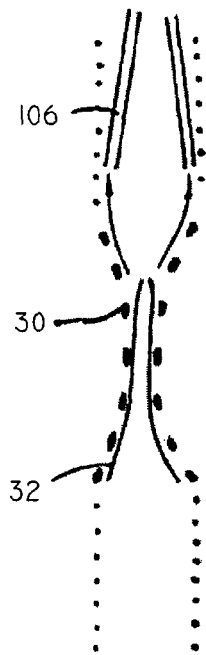
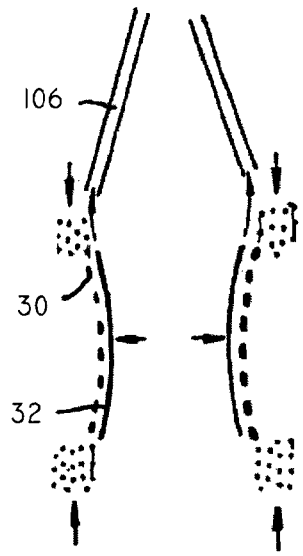
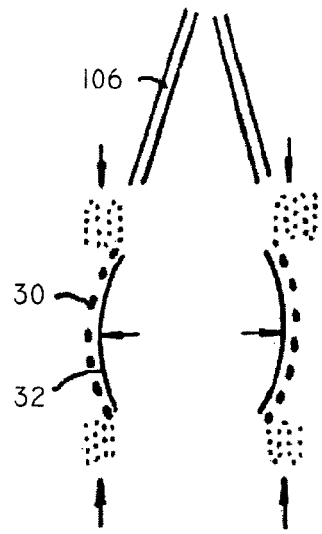
FIG 13A　　　　　FIG 13B　　　　　FIG 13C
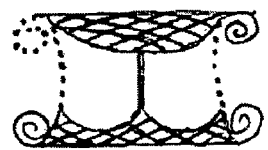
FIG 13D　　　　　FIG 13E

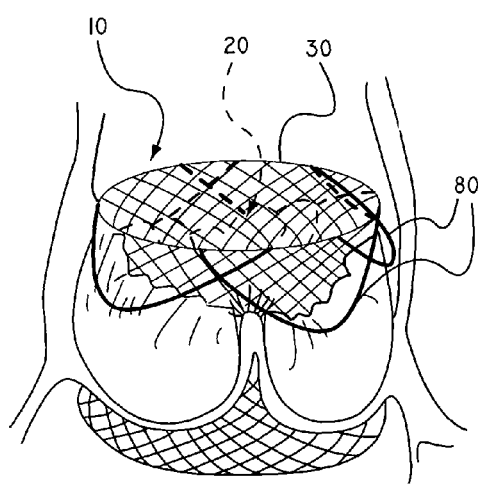 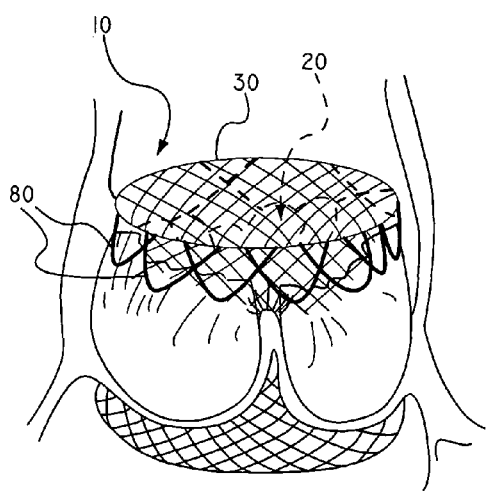
FIG 17AFIG 17B

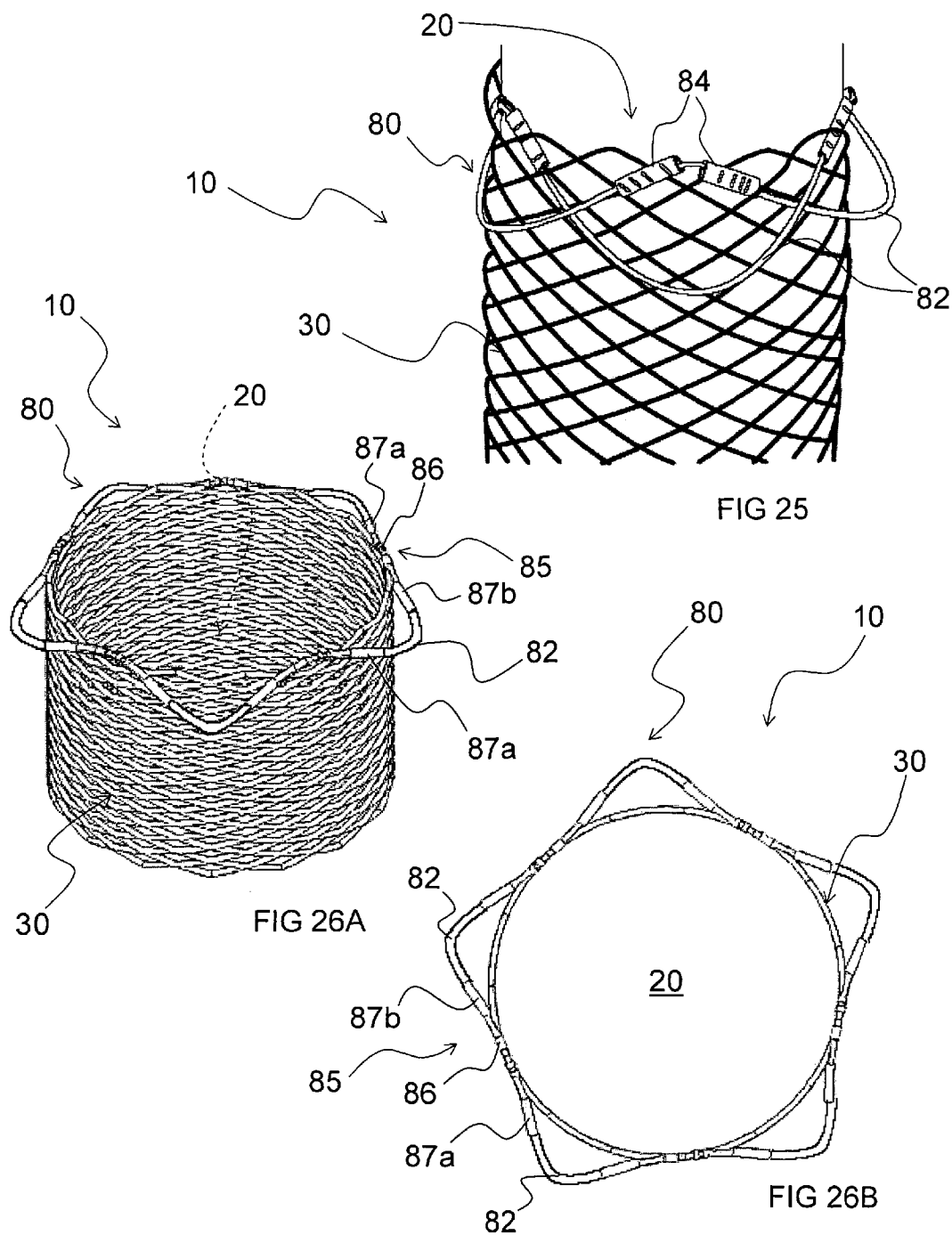

METHODS AND APPARATUS FOR ENDOVASCULAR HEART VALVE REPLACEMENT COMPRISING TISSUE GRASPING ELEMENTS

CROSS-REFERENCE

This application is a continuation-in-part application of application Ser. No. 10/972,287, filed Oct. 21, 2004, which is a continuation-in-part of application Ser. No. 10/746,240, filed Dec. 23, 2003, now abandoned both of which are incorporated herein by reference in their entireties and to which applications we claim priority under 35 USC §120.

BACKGROUND OF THE INVENTION

The present invention relates to methods and apparatus for endovascularly replacing a heart valve. More particularly, the present invention relates to methods and apparatus for endovascularly replacing a heart valve with a replacement valve using an expandable anchor and tissue grasping elements.

Heart valve surgery is used to repair or replace diseased heart valves. Valve surgery is an open-heart procedure conducted under general anesthesia. An incision is made through the patient's sternum (sternotomy), and the patient's heart is stopped while blood flow is rerouted through a heart-lung bypass machine.

Valve replacement may be indicated when there is a narrowing of the native heart valve, commonly referred to as stenosis, or when the native valve leaks or regurgitates. When replacing the valve, the native valve is excised and replaced with either a biologic or a mechanical valve. Mechanical valves require lifelong anticoagulant medication to prevent blood clot formation, and clicking of the valve often may be heard through the chest. Biologic tissue valves typically do not require such medication. Tissue valves may be obtained from cadavers or may be porcine or bovine, and are commonly attached to synthetic rings that are secured to the patient's heart.

Valve replacement surgery is a highly invasive operation with significant concomitant risk. Risks include bleeding, infection, stroke, heart attack, arrhythmia, renal failure, adverse reactions to the anesthesia medications, as well as sudden death. 2-5% of patients die during surgery.

Post-surgery, patients temporarily may be confused due to emboli and other factors associated with the heart-lung machine. The first 2-3 days following surgery are spent in an intensive care unit where heart functions can be closely monitored. The average hospital stay is between 1 to 2 weeks, with several more weeks to months required for complete recovery.

In recent years, advancements in minimally invasive surgery and interventional cardiology have encouraged some investigators to pursue percutaneous replacement of the aortic heart valve. However, the current devices suffer from several drawbacks.

First, many of the devices available today can become mispositioned with respect to the native valve. This misposition may arise for a number of reasons, such as: the valve slipping after placement, improper initial positioning arising from the difficulties associated with visualizing the relative positions of the native and prosthetic valve, the difficulty in transmitting tactile feedback to the user through the delivery tool. This is a critical drawback because improper positioning too far up towards the aorta risks blocking the coronary ostia of the patient. Furthermore, a misplaced stent/valve in the other direction (away from the aorta, closer to the ventricle) will impinge on the mitral apparatus and eventually wear through the leaflet as the leaflet continuously rubs against the edge of the stent/valve.

Moreover, some stent/valve devices simply crush the native valve leaflets against the heart wall and do not grasp or engage the leaflets in a manner that would provide positive registration of the device relative to the native position of the valve. This increases an immediate risk of blocking the coronary ostia, as well as a longer-term risk of migration of the device post-implantation.

Another drawback of the devices known today is that during implantation they may still require the patient to be on life support as the valve does not function for a portion of the procedure. This further complicates the implantation procedure.

In view of drawbacks associated with previously known techniques for endovascularly replacing a heart valve, it would be desirable to provide methods and apparatus that overcome those drawbacks.

SUMMARY OF THE INVENTION

One aspect of the invention provides an apparatus for endovascularly replacing a patient's heart valve. The apparatus includes: an expandable anchor supporting a replacement valve, the anchor and replacement valve being adapted for percutaneous delivery and deployment to replace the patient's heart valve. The anchor comprises a braid having grasping elements adapted to grasp tissue in a vicinity of the patient's heart valve. The grasping elements preferably are atraumatic.

Another aspect of the invention provides an apparatus for endovascularly replacing a patient's heart valve, including: an expandable anchor supporting a replacement valve, the anchor and replacement valve being adapted for percutaneous delivery and deployment to replace the patient's heart valve, the anchor comprising grasping elements adapted to grasp tissue in a vicinity of the patient's heart valve. The anchor is self-expanding and has a delivery configuration, an at-rest configuration and a deployed configuration, the at-rest configuration having a diameter larger than a diameter of the delivery configuration and smaller than a diameter of the deployed configuration. The grasping elements are positioned substantially parallel with the anchor in the delivery configuration, at a first angle with the anchor in the at-rest configuration and at a second angle with the anchor in the deployed configuration.

Yet another aspect of the invention provides a method for endovascularly replacing a patient's heart valve, the method including: endovascularly delivering an anchor and a replacement valve supported within the anchor to a vicinity of the heart valve in a collapsed delivery configuration, the anchor comprising grasping elements adapted to grasp tissue in a vicinity of the heart valve; expanding the anchor, thereby rotating the grasping elements; and grasping the tissue with the rotating grasping elements.

In some embodiments, the tissue comprises leaflets of the patient's heart valve. When the grasping elements grasp the leaflets, the anchor is substantially distal to the coronary ostia of the patient. Moreover, once grasped, the grasping elements prevent the distal movement of the anchor. In some embodiments, the grasping elements are integral with the anchor or part of the anchor. In other embodiments, the grasping elements are attached to the proximal region of the anchor.

In some embodiments the tissue comprises an annulus of the patient's heart valve. When the grasping elements grasp the annulus, the anchor is substantially proximal of the mitral apparatus. Moreover, once grasped, the grasping elements prevent the proximal movement of the anchor. In some embodiments, the grasping elements are integral with the anchor or part of the anchor. In other embodiments, the grasping elements are attached to the distal region of the anchor.

In any of the embodiments described herein, the grasping elements or the step of grasping the tissue may provide a locating function for properly placing the apparatus. This locating function may be accomplished without necessitating a precise placement of the replacement valve, especially in embodiments that comprise both proximal and distal grasping elements, e.g., that grasp both the valve leaflets and the valve annulus. This locating function advantageously may be accomplished without necessitating tactile feedback regarding the positioning of the replacement valve.

Additionally, in any of the embodiments described herein, the anchor may be adapted for active expansion during deployment. Active expansion can occur by actuating proximal and/or distal actuation elements of the anchor. The anchor may be configured for locking and may include a locking element. The replacement valve is situated within the anchor and is adapted to permit blood flow and prevent blood backflow both during and after deployment.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 1A and 1B are schematic views of an anchor and valve apparatus in accordance with the present invention. FIG. 1A illustrates the apparatus in a collapsed delivery configuration within a delivery system. FIG. 1B illustrates the apparatus in an expanded configuration partially deployed from the delivery system.

FIGS. 4A-4O are schematic detail views illustrating exemplary end turns for a braided anchor.

FIGS. 11A-11D are schematic side views of various braided anchor configurations.

FIGS. 13A-13E are schematic views of different weave configurations for an anchor braid.

FIGS. 17A and 17B illustrate variations of the apparatus of FIG. 15 comprising alternative grasping elements deployed across a patient's native valve.

FIG. 25 illustrates alternative grasping elements that are attached to the anchor.

FIGS. 26A-26B illustrate a variation of the attached grasping elements of FIG. 25.

DETAILED DESCRIPTION OF THE INVENTION

The present invention relates to an apparatus and methods for endovascularly delivering and deploying an aortic prosthesis within a patient's native heart valve, referred to hereinafter as "replacing" a patient's heart valve. The delivery system includes a sheath assembly, a multi-lumen shaft, and a guide wire for placing the apparatus endovascularly within a patient and a user control allowing manipulation of the aortic prosthesis. The apparatus includes an anchor and a replacement valve. The anchor and the replacement valve are adapted for percutaneous delivery and deployment within a patient's heart valve.

In some embodiments, the apparatus includes engagement elements and/or a seal inverting element situated along a proximal region of the anchor. The engagement elements are adapted to engage the native leaflets of the patient's heart, or more preferably the proximal edge and/or the commissural attachments of the native leaflets. The engagement elements need not extend all the way into the pocket or the distal end of the native leaflet. The apparatus additionally or alternatively may comprise engagement elements along a distal region of the anchor for engaging an annulus of the native valve. The engagement elements may be formed integrally with the anchor or may be attached to the anchor.

In some embodiments, the proximal and/or distal engagement elements comprise grasping elements configured to grasp tissue in the vicinity of the patient's heart valve, e.g. to rotate into the tissue and secure the apparatus relative to the tissue. The grasping elements preferably are atraumatic. Preferred embodiments of the apparatus are depicted in FIGS. 1-27, which are discussed in more detail below.

Figure 1A:
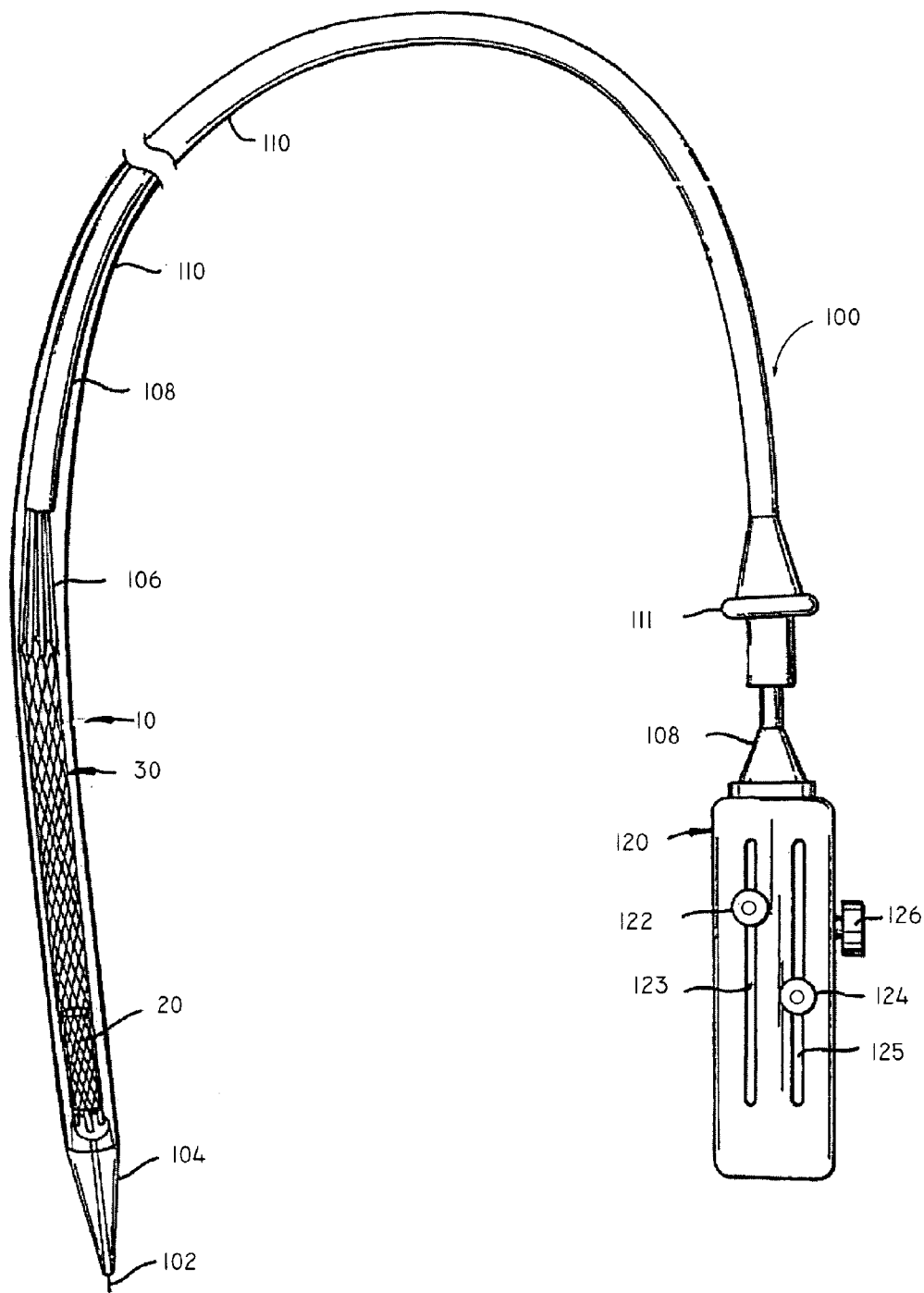

FIGS. 1A and 1B illustrate one embodiment of a delivery system and the apparatus of the present invention.

As illustrated by FIG. 1A, apparatus 10 comprising replacement valve 20 and anchor 30 may be collapsed for delivery within a delivery system 100. Delivery system 100 includes a guidewire 102, a nosecone 104, anchor actuation elements 106 (e.g., "fingers") coupled to a multi-lumen shaft 108, an external sheath 110 having a proximal handle 111, and a control handle 120. Delivery system 100 further comprises distal region control elements (not shown) comprised of, or actuated by, control wires (not shown), which pass through one or more lumens of shaft 108 and are reversibly coupled to posts 32 of anchor 30 for manipulating a distal region of apparatus 10. Thus, the distal region control elements may function as a distal actuation element. The control wires may comprise, for example, strands of suture, or metal or polymer wires.

The delivery system also comprises proximal region control elements that are comprised of, or actuated by, additional control wires that pass through one or more lumens of shaft 108 and anchor actuation elements 106. The wires reversibly couple the anchor actuation elements to a proximal region of anchor 30. In some embodiments, the anchor actuation elements and associated wires may be referred to as proximal actuation elements.

Control handle 120 is coupled to multi-lumen shaft 108. A knob 122 disposed in slot 123 is coupled to the distal region control wires for controlling movement of the distal region of apparatus 10. Likewise, a knob 124 disposed in slot 125 is coupled to the proximal region control wires for control of the proximal region of apparatus 10. Handle 120 may also have a knob 126 for, e.g., decoupling the proximal and/or distal region control wires from apparatus 10, or for performing other control functions.

Figure 2:
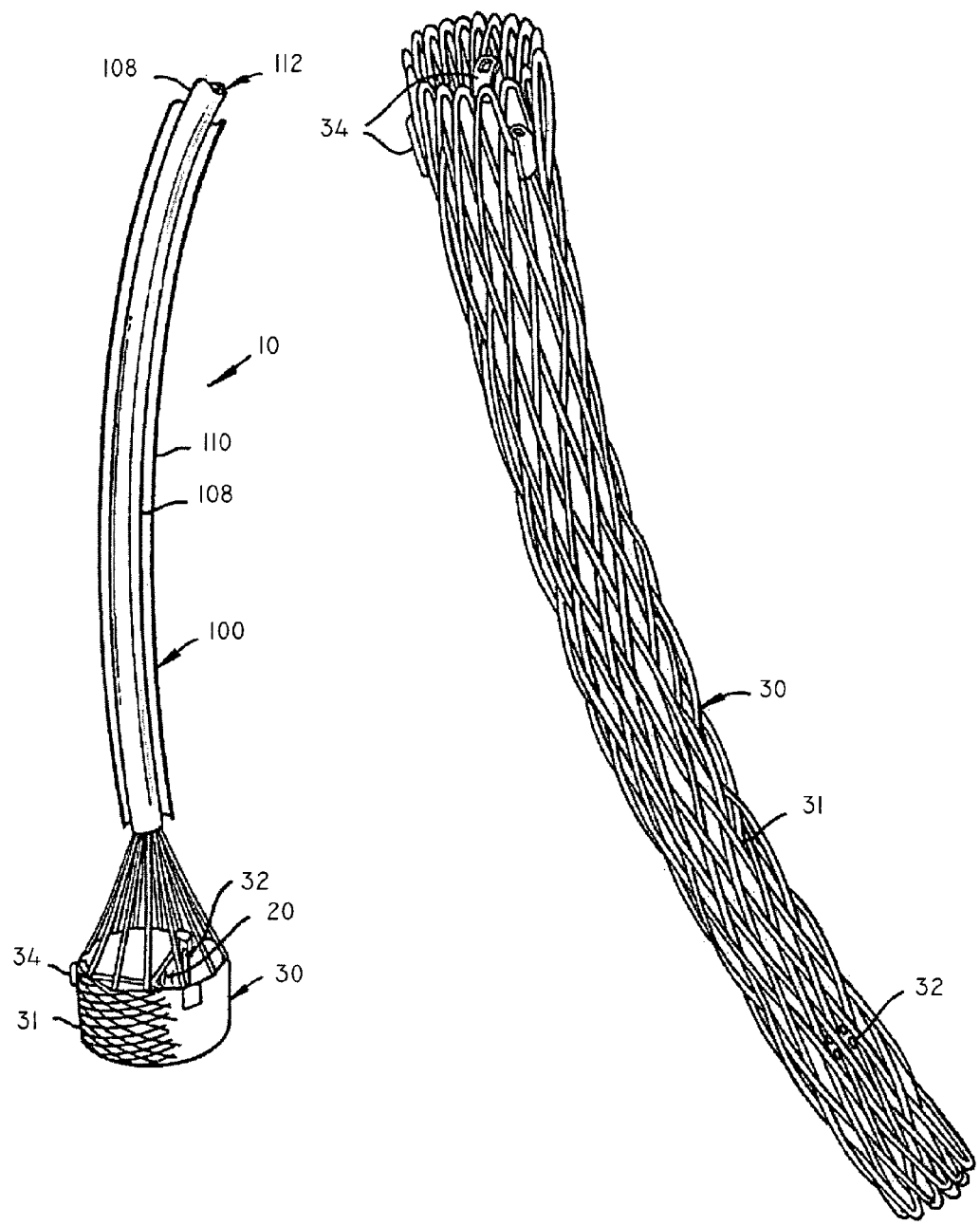
FIG. 2 illustrates an anchor of FIG. 1 in the collapsed delivery configuration with locking elements separated.

As illustrated by FIG. 1B, apparatus 10 comprises an anchor 30 and a replacement valve 20. Anchor 30 preferably comprises a braid. Such braid can have closed ends at either or both of its ends but preferably at least in its proximal end. Replacement valve 20 is preferably coupled to the anchor at posts 32 attached at a distal region of the anchor. Thus, posts 32 may function as a valve support and may be adapted to support the replacement valve within the anchor. In the embodiment shown, there are three posts, corresponding to the valve's three commissure attachments. The posts can be attached to the braid of anchor 30. The posts can be attached to the braid's distal region, as shown in FIG. 2, central region, or proximal region. Replacement valve 20 can be composed of a metal, a synthetic material and/or may be derived from animal tissue. Replacement valve 20 is preferably configured to be secured within anchor 30.

In preferred embodiments, anchor 30 is collapsible and/or expandable and is formed from material such as Nitinol™, cobalt-chromium steel or stainless steel wire. More preferably, an anchor 30 is self-collapsing and/or self-expanding and is made out of shape memory material, such as Nitinol™. An anchor composed of shape memory material may self-expand to or toward its "at-rest" configuration. This "at rest" configuration of an anchor can be, for example its expanded configuration, its collapsed configuration, or a partially expanded configuration (between the collapsed configuration and the expanded configuration). In some embodiments, an anchor's at-rest configuration is between its collapsed configuration and its expanded configuration. Depending on the "at rest" diameter of the anchor and the diameter of the patient's anatomy at the chosen deployment location, the anchor may or may not self-expand to come into contact with the diameter of the patient's anatomy at that location.

Anchor 30 may be expanded to a fully deployed configuration from a partial deployed configuration (e.g., self-expanded or at-rest configuration) by actively expanding, e.g., actively foreshortening, anchor 30 during endovascular deployment. Active foreshortening is described in more detail in U.S. patent application Ser. No. 10/746,280, which is incorporated herein by reference in its entirety. During active foreshortening, the distal region of anchor 30 may be pulled proximally via a proximally directed force applied to posts 32 via a distal deployment system interface comprised of the distal system control elements. The distal deployment system interface is adapted to expand radially during application of a proximally directed force on the distal end of the anchor when opposed by a distally directed force applied to the proximal end of the anchor, e.g., by the anchor actuation elements 106.

In some embodiments, actuating foreshortening of the apparatus involves applying a proximally directed force on a deployment system interface at the distal end of the anchor, while maintaining the proximal end of the anchor in the same location. In other embodiments, foreshortening of the apparatus involves applying a distally directed force on proximal end of the anchor (e.g., by applying a distally directed force on the anchor actuation elements).

Anchor actuation elements 106 (e.g., fingers, tubes, posts, and control wires connecting to posts) are preferably adapted to expand radially as the anchor expands radially and to contract radially as the anchor contracts radially. Furthermore, proximally or distally directed forces by the anchor actuation elements on one end of the anchor do not diametrically constrain the opposite end of the anchor. In addition, when a proximally or distally directed force is applied on the anchor by the anchor actuation elements, it is preferably applied without passing any portion of a deployment system through a center opening of the replacement valve. This arrangement enables the replacement valve to operate during deployment and before removal of the deployment system.

The distal deployment system interface may include control wires that are controlled, e.g., by control knob 122 of control handle 120. Similarly, the proximal regions of anchor 30 may be pushed distally via a proximal deployment system interface at the proximal end of the anchor. The proximal deployment system interface is adapted to permit the deployment system to apply a distally directed force to the proximal end of anchor 30 through, e.g., anchor actuation elements 106, which are controlled by, e.g., control knob 124 of control handle 120. The proximal deployment system interface may be further adapted to expand radially during application of a distally directed force on the proximal end of the anchor. Such active expansion of the anchor optionally may be assisted via inflation of a balloon catheter (not shown) reversibly disposed within apparatus 10, as described in U.S. patent application Ser. No. 10/746,280.

Once anchor 30 is fully deployed, posts 32 and buckles 34 of anchor 30 may be used to lock and maintain the anchor in the deployed configuration. In one embodiment, the control wires attached to posts 32 are threaded through buckles 34 so that the proximally directed force exerted on posts 32 by the control wires during deployment pulls the proximal locking end of posts 32 toward and through buckles 34. Such lock optionally may be selectively reversible to allow for repositioning and/or retrieval of apparatus 10 during or post-deployment. Apparatus 10 may be repositioned or retrieved from the patient until the two-part locking mechanism of posts 32 and buckles 34 of anchor 30 have been actuated. When the lock is selectively reversible, the apparatus may be repositioned and/or, retrieved as desired, e.g., even after actuation of the two-part locking mechanism. Once again, further details of this and other anchor locking structures may be found in U.S. patent application Ser. No. 10/746,280. Locking mechanisms used herein may also include a plurality of levels of locking wherein each level of locking results in a different amount of expansion of anchor 30. For example, the proximal end of the post can have multiple configurations for locking within the buckle wherein each configuration results in a different amount of anchor expansion. FIG. 2 illustrates a braided anchor of FIG. 1 in the collapsed delivery configuration with locking elements separated.

Figure 3:
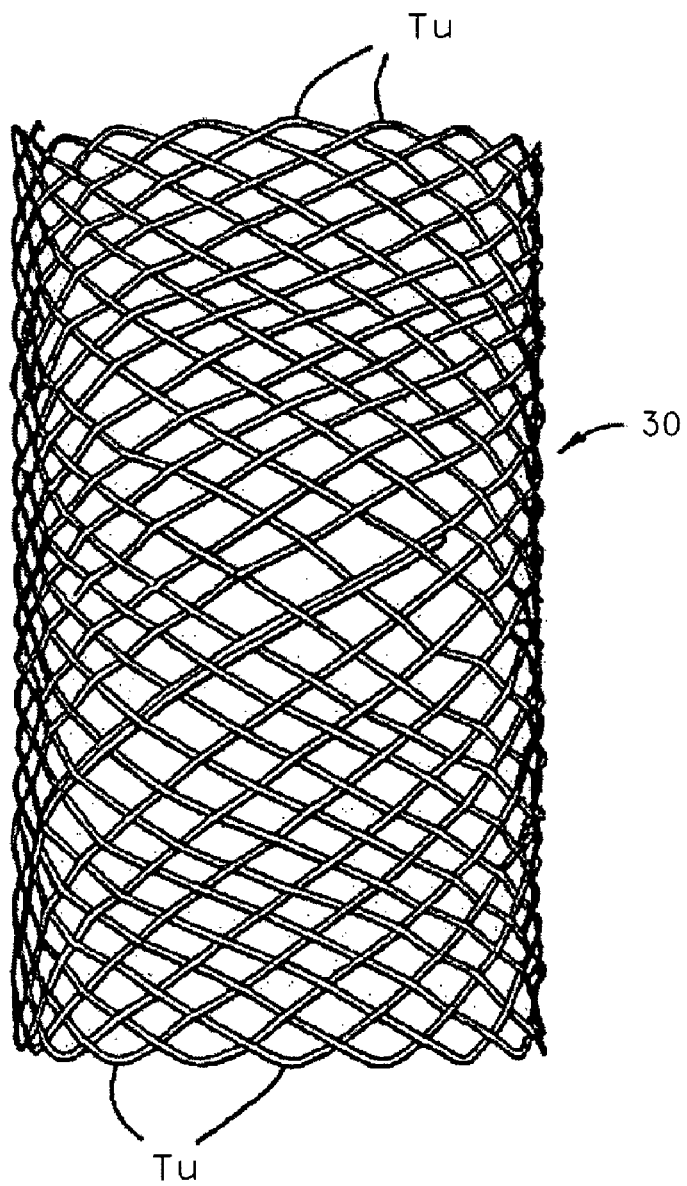
FIG. 3 illustrates a braided anchor of the present invention with closed end turns Tu.

FIG. 3 provides a detail view of a front side region of anchor braid 30 with closed end turns Tu. Anchor braid 30 includes various cells, some having an end turn Tu. End turns can serve various functions. For example, end turns can be configured to reduce the sheathing force, to reduce stress within the braid during delivery and deployment, to prevent migration during expansion of the anchor, to positively register the anchor against the native valve during deployment. In preferred embodiments, an end turn feature functions to prevent migration and to register the anchor by engaging the native leaflets and/or the annulus of the native valve. In preferred embodiments, the proximal region or the distal region of anchor 30 comprises embodiments (Tu). In some embodiments, the end turn feature grasps tissue in the vicinity of the native heart valve, such as the native valve leaflets and/or the valve annulus, e.g., by rotating into the tissue during expansion of the anchor.

FIGS. 4A-4N provide multiple examples of edge cells having an end turn feature. The end turn features disclosed and others known in the art may be used as engagement or grasping elements to engage and/or grasp tissue in the vicinity of a patient's heart valve, such as the native heart leaflets or the valve annulus, with the anchor. The engagement or grasping elements may be integral with the anchor, for example, may be part of a braided anchor. Alternatively, the engagement or grasping elements may be attached to the anchor, for example, via interweaving, crimping, welding, soldering, wire wrapping, or other suitable attachment means. The end turn features can occur at the proximal, central, or distal region of the anchor, or a combination thereof.

For example, FIG. 4A illustrates a detail view of a standard end turn Tu in an anchor braid resulting in a braid with substantially uniform cell size and shape.

FIG. 4B illustrates a turn that has been elongated to lengthen the distance over which forces concentrated in the turn may be distributed, resulting in an anchor braid having edge cells that are longer along the anchor axis than the other cells defined by the braid. This elongated turn feature may be formed by routing the wire of braid about outer posts and then heat setting the wire.

FIG. 4C illustrates an alternative anchor edge cell configuration, wherein the tip of the elongated wire turn may be bent out of a cylindrical shape defined by the braid of anchor braid 30. This may be achieved, for example, via a combination of routing of wire W within a fixture and then heat setting. Such a turn Tu in the anchor edge cells in FIG. 4C may reduce stress in some configurations without increasing height, and may also provide a lip for engaging or grasping the patient's native valve leaflets to facilitate proper positioning of apparatus 10 during deployment.

In FIG. 4D, a W-shaped turn feature has been formed at the wire turn, e.g., by routing the wire of anchor braid 30 about a central inner post and two flanking outer posts. As with the elongated braid cells of FIGS. 4B and 4C, the W-shape may better distribute stress about turn Tu.

The anchor edge cell configuration in FIG. 4E includes a loop formed in braid 30 at the turn, which may be formed by looping wire W around an inner or outer post.

FIG. 4F provides another alternative anchor edge cell configuration having a figure-eight shape. Such a shape may be formed, for example, by wrapping wire W about an inner post and an aligned outer post in a figure-eight fashion, and then heat setting the wire in the resultant shape.

In FIG. 4G, the edge cells of braid 30 include a heart-shaped configuration, which may be formed by wrapping the wire about an aligned inner and outer post in the desired manner.

In FIG. 4H, the edge cells of braid 30 have an asymmetric loop at turn Tu. The asymmetric loop will affect twisting of braid 30 during expansion and collapse of the braid, in addition to affecting stress concentration.

In FIG. 4I, the anchor edge cells have a double-looped turn configuration, e.g. via wrapping about two adjacent inner or outer posts. Additional loops may also be employed.

The double loop turn feature may be formed with a smooth transition between the loops, as in FIG. 4I, or may be heat set with a more discontinuous shape, as in FIG. 4J.

FIG. 4K illustrates that the edge cells of braid 30 may have multiple different configurations about the anchor's circumference. For example, the anchor edge cells shown in FIG. 4K have extended length cells as in FIG. 4B disposed adjacent to standard size edge cells, as in FIG. 4A.

The anchor edge cells of FIG. 4L have an extended turn configuration having an extended loop.

The anchor edge cells shown in FIG. 4M have an alternative extended configuration with a specified heat set profile.

In FIG. 4N, some or all anchor edge cells are interwoven. When interwoven, one or more edge cells may be shorter or longer than an adjacent edge cell. This permits one or more edge cells to extend into one or more leaflet pocket(s). For example, in FIG. 4N the middle Tu may be taller than the two adjacent edge cells thus permitting the edge cell to be situated within a leaflet pocket, In any of the embodiments herein, edge cells may be wrapped using wire, string, or sutures, at a location where the wire overlaps after an end turn as is illustrated in FIG. 4O. This tied-end turn feature prevents cells from interlocking with each other during deployment.

The anchor and any of its features may be heat set at different configurations. For example, the anchor may be heat set at its "at-rest" configuration such that upon unsheathing it expands radially. The end turn features/leaflet engagement elements may be heat set at a different "at-rest" configuration than the rest of the anchor. In some embodiments, the end turn features are heat set to "flower" and then "evert" upon unsheathing. In other embodiments, the end turns are heat set in an everted configuration and lie parallel/radially concentric with the anchor, e.g., lie substantially flat against the anchor, in the sheathed delivery configuration and then to expand outward upon unsheathing. When used as grasping elements, the end turns may rotate relative to the anchor during active expansion of the anchor in order to grasp tissue in the vicinity of the patient's heart valve.

The end turn features of FIG. 4 are provided only for the sake of illustration and should in no way be construed as limiting. Additional turn features within the scope of the present invention will apparent to those of skill in the art in view of FIG. 4. Furthermore, combinations of any such end turn features may be provided to achieve the desired characteristics of anchor 30.

Figure 5A:
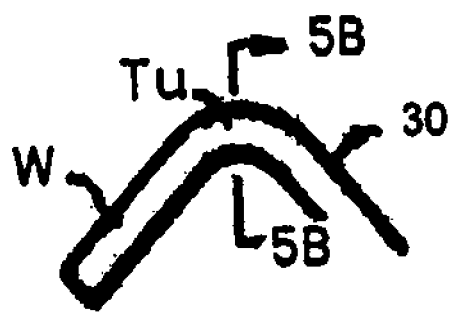
FIGS. 5A-5E illustrate additional features for end turns of a braided anchor.
Figure 5B:
Figure 5C:
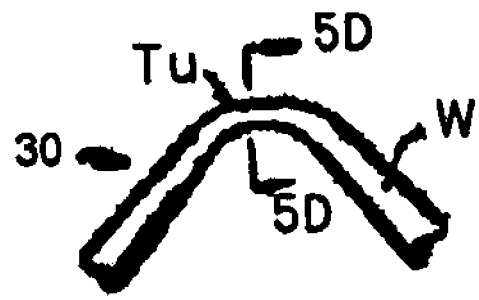

Referring now to FIGS. 5A-E, additional configurations for reducing stress concentration and/or circumferential stiffness of an anchor braid and/or engagement/grasping elements are illustrated. Such configurations can be used independently or in conjunction with other configurations disclosed herein. Such configurations are preferably used at the anchor's edges to locally reduce the cross-sectional area of substantially all cells or of substantially all cells in the anchor braid's edge (e.g., proximal and/or distal). As seen in FIGS. 5A and 5B, turns Tu in wire W typically may have a substantially continuous (e.g., round) cross-sectional profile. As seen in FIG. 5C, modifying the edge cell configuration by locally reducing the thickness or cross-sectional area of wire W at turn(s) Tu will reduce stress concentration within the wire at the turns and facilitate collapse and/or expansion of anchor braid 30 from the delivery to the deployed configurations. Furthermore, it is expected that such localized reduction in thickness or cross-sectional area will reduce a risk of kinking, fatigue or other failure at turns Tu.

Figure 5D:
Figure 5E:

In any of the embodiments herein, localized reduction of an anchor wire may be achieved via a localized etching and/or electropolishing process. Alternatively or additionally, localized grinding of the turns may be utilized. Additional processing techniques will be apparent to those of skill in the art. As seen in FIGS. 5D-5E, wire W may, for example, comprise an oval or rectangular cross-sectional profile, respectively, after localized reduction. The wire alternatively may comprise a round profile of reduced cross-sectional area (not shown). Additional profiles will be apparent. Localized reduction can take place at any time (e.g., before or after a braid is woven). Preferably, localized reduction occurs after weaving. However, in some embodiments, a wire of a given length may be etched or ground at preset segments and subsequently woven.

With reference now to FIGS. 6A-F, a method of endovascularly replacing a patient's diseased aortic valve within heart H is provided. Left ventricle LV is also illustrated. The method involves endovascularly delivering an anchor/valve apparatus and properly positioning such apparatus via positive registration with the patient's native valve leaflets. Registration with the native valve leaflet occurs using at least one leaflet engagement element.

Figure 6A:
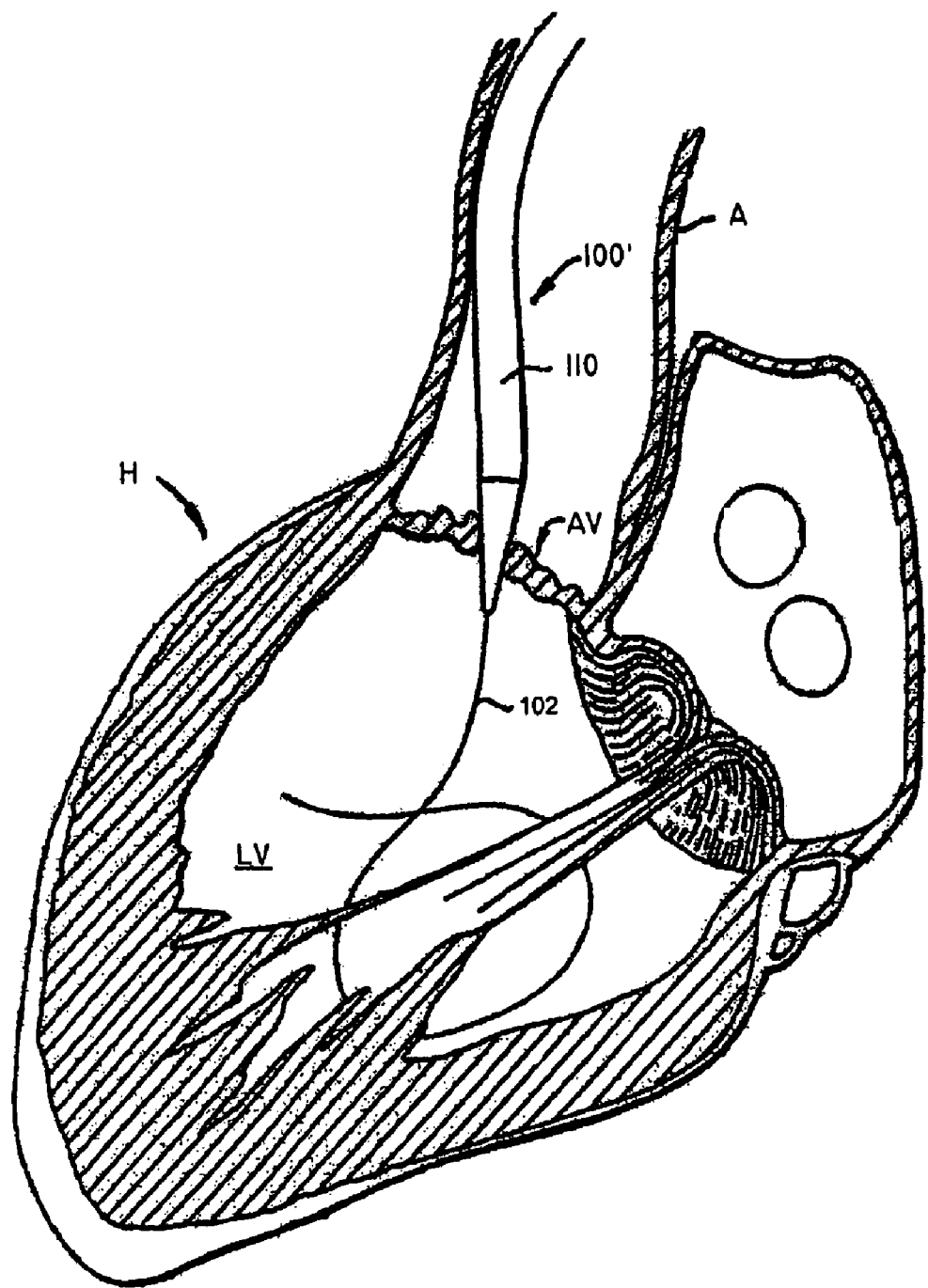
FIGS. 6A-6F illustrate deployment of an anchor with leaflet engagement elements on the deployment system.

In FIG. 6A, modified delivery system 100' delivers apparatus 10 to diseased aortic valve AV within sheath 110. Apparatus 10 is delivered in a collapsed delivery configuration within lumen 112 of the sheath.

Figure 6B:
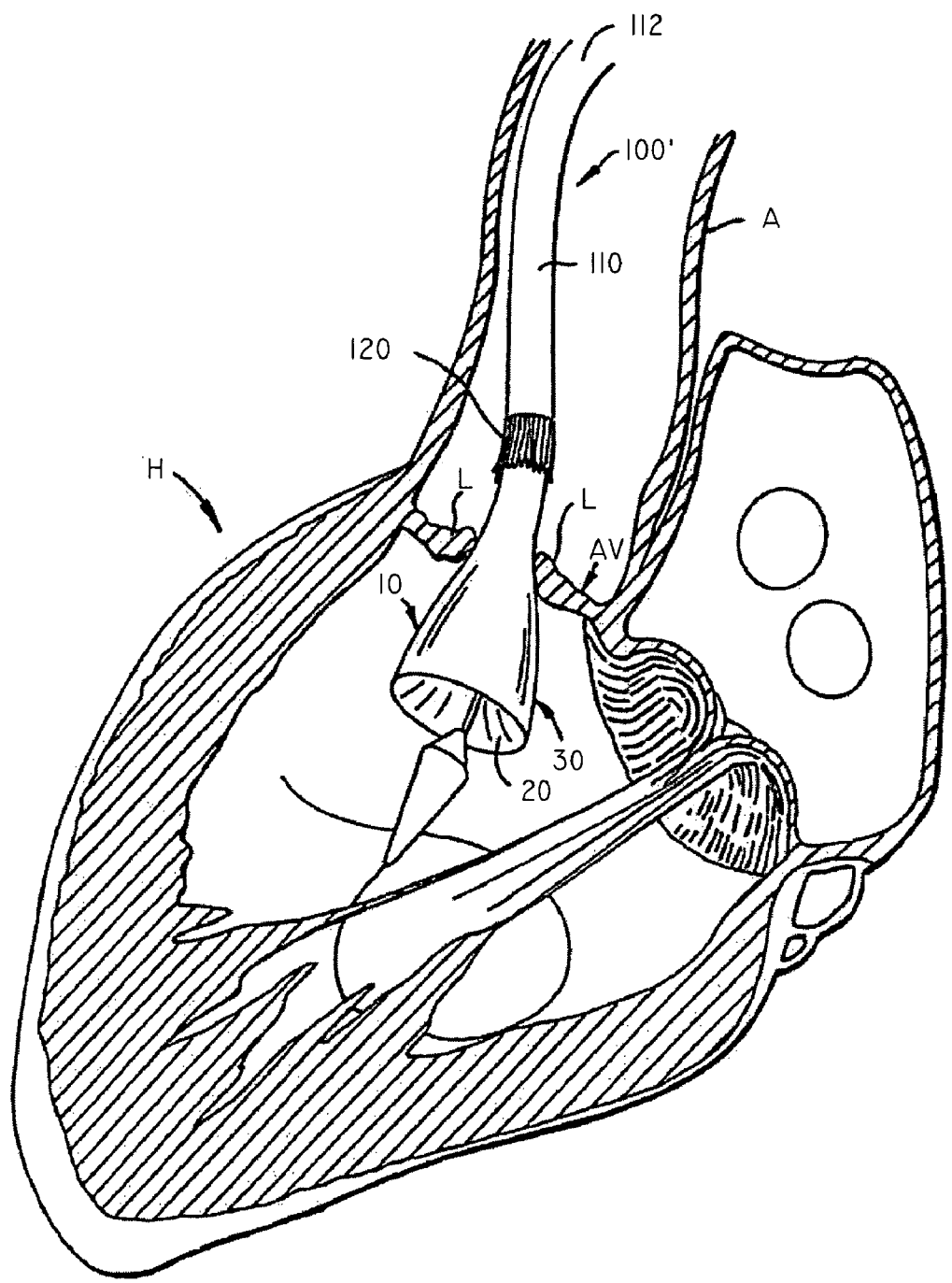
Figure 6C:
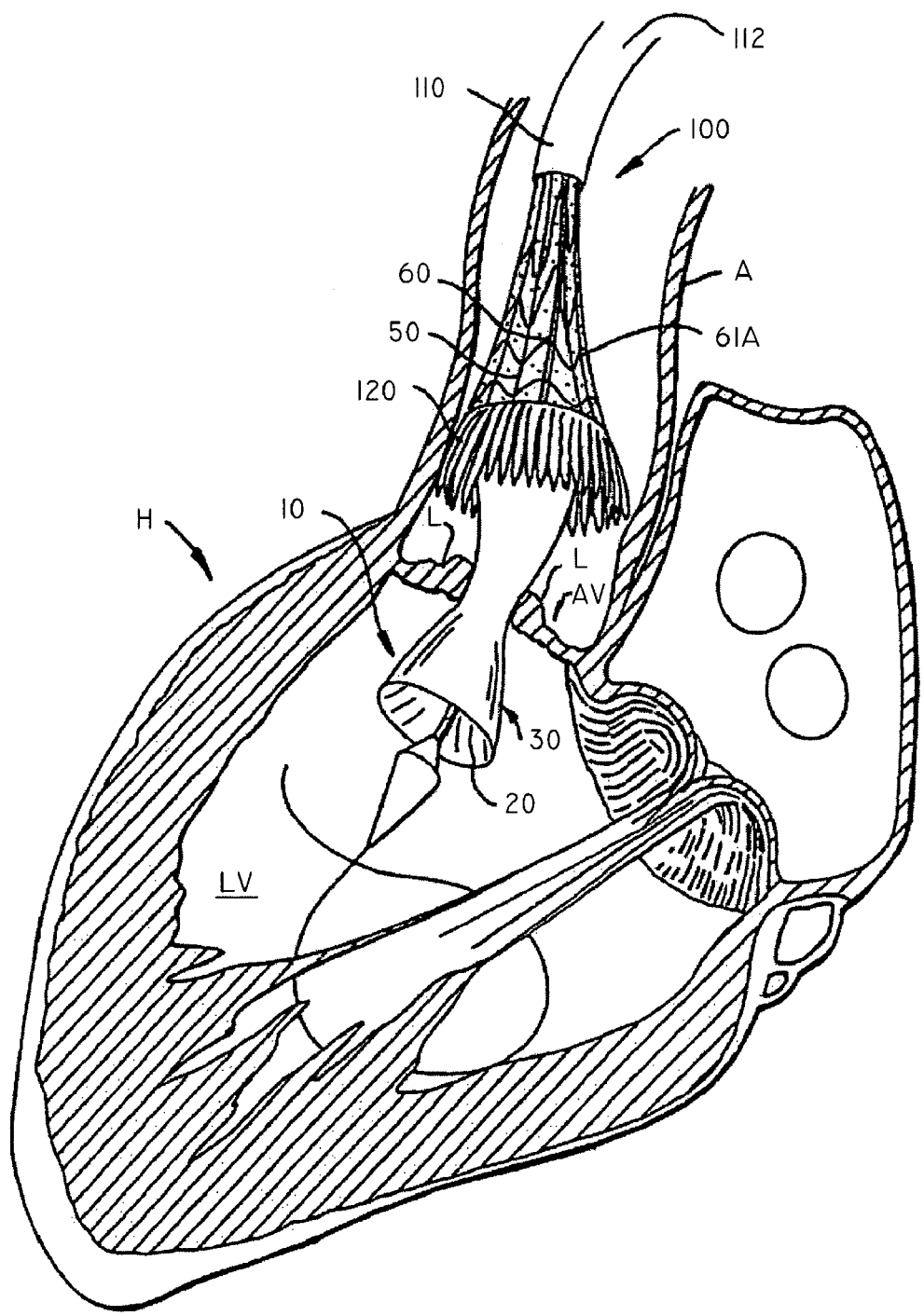

As seen in FIGS. 6B and 6C, apparatus 10 is deployed from lumen 112 of sheath 110, for example, under fluoroscopic guidance. Sheath 110 includes at its distal end leaflet engagement elements 120. Upon deployment, anchor 30 of apparatus 10 dynamically self-expands to a partially deployed or at-rest configuration. This causes the anchor actuation elements, illustratively tubes 60, to also dynamically expand, as well as membrane filter (or braid) 61A and leaflet engagement elements 120. As when deployed via delivery system 100, deployment of apparatus 10 via delivery system 100' is fully reversible until locks 40 have been actuated.

Leaflet engagement elements 120 preferably self-expand along with anchor 30. In preferred embodiments, the distal ends of leaflet engagement elements 120 expand a greater radial distance than anchor 30. Moreover, engagement elements 120 may be disposed between tubes 60 of delivery system 100' and a proximal region of anchor 30. However, leaflet engagement elements 120 may also be disposed, e.g., attached or coupled, on the proximal region of the anchor (as is illustrated in FIG. 7). In FIG. 6, leaflet engagement elements 120 releasably engage the anchor. As seen in FIG. 6C, the leaflet engagement elements 120 are initially deployed proximal of the patient's native valve leaflets L. Apparatus 10 and elements 120 then may be advanced, i.e., dynamically repositioned, until engagement elements positively register against the leaflets, thereby ensuring proper positioning of apparatus 10. The leaflet engagement elements engage with the proximal edges of the native valve leaflets and/or with the commissural attachments. The leaflet engagement elements need not extend all the way to the distal edge of the native leaflets (the leaflet pockets). In preferred embodiments, a leaflet engagement element length is less than about 20 mm, more preferably less than about 15 mm, or more preferably less than about 10 mm. Once leaflet engagement elements 120 are registered against the native valve leaflets and/or commissural attachments, apparatus 10 deploys substantially distal to the coronary ostia of the heart.

In any of the embodiments herein, the delivery system optionally can include filter structure 61A (e.g., a filter membrane or braid) as part of the anchor actuation elements, such as push tubes 60, to act as an embolic protection element. Emboli can be generated during manipulation and placement of an anchor from either diseased native leaflet(s) or surrounding aortic tissue, and can cause blockage. Arrows 61B in FIG. 6E show blood flow through filter structure 61A where blood is allowed to flow, but emboli are trapped in the delivery system and removed with it at the end of the procedure.

Figure 6D:
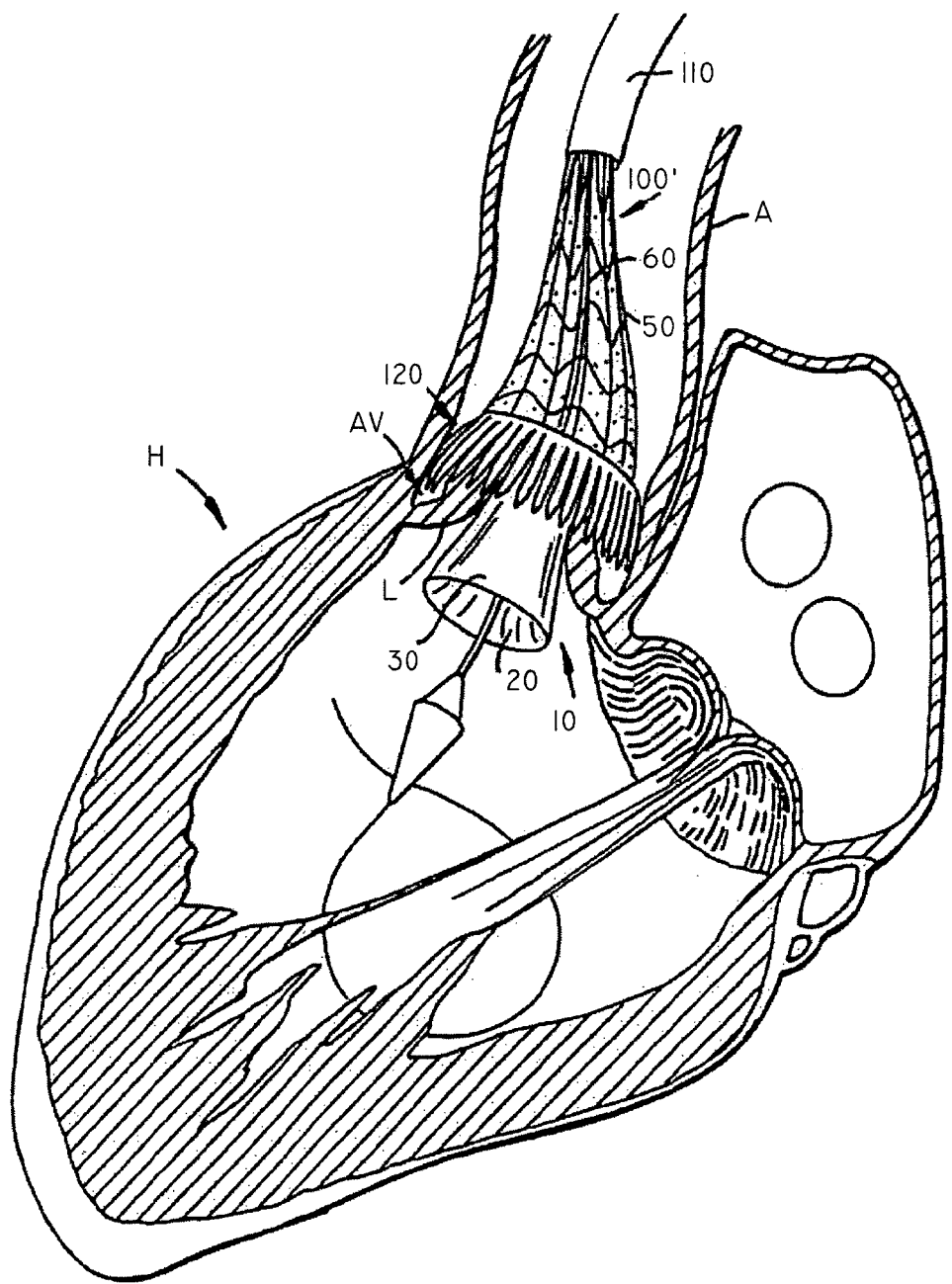
Figure 6E:
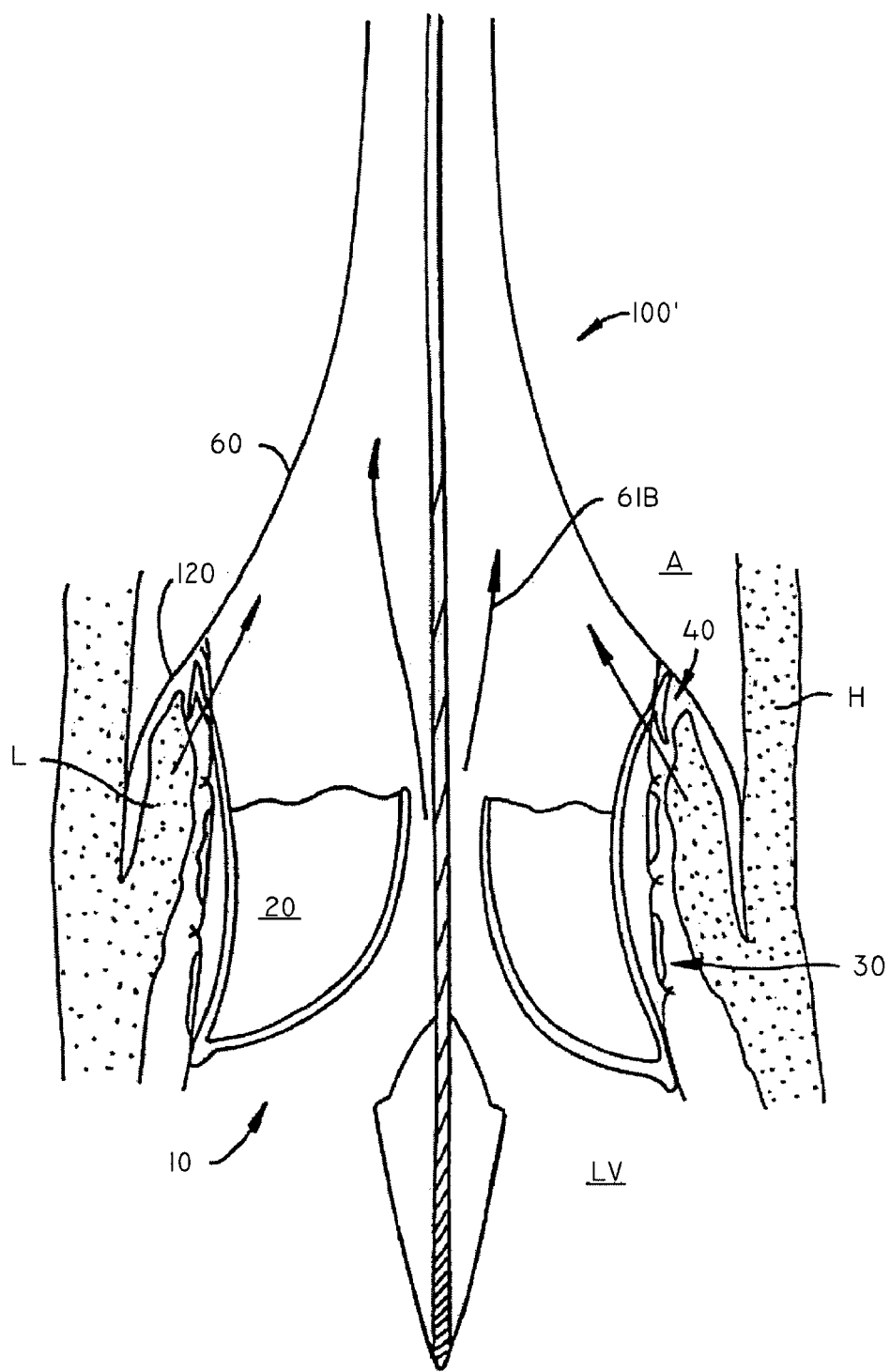
Figure 7:
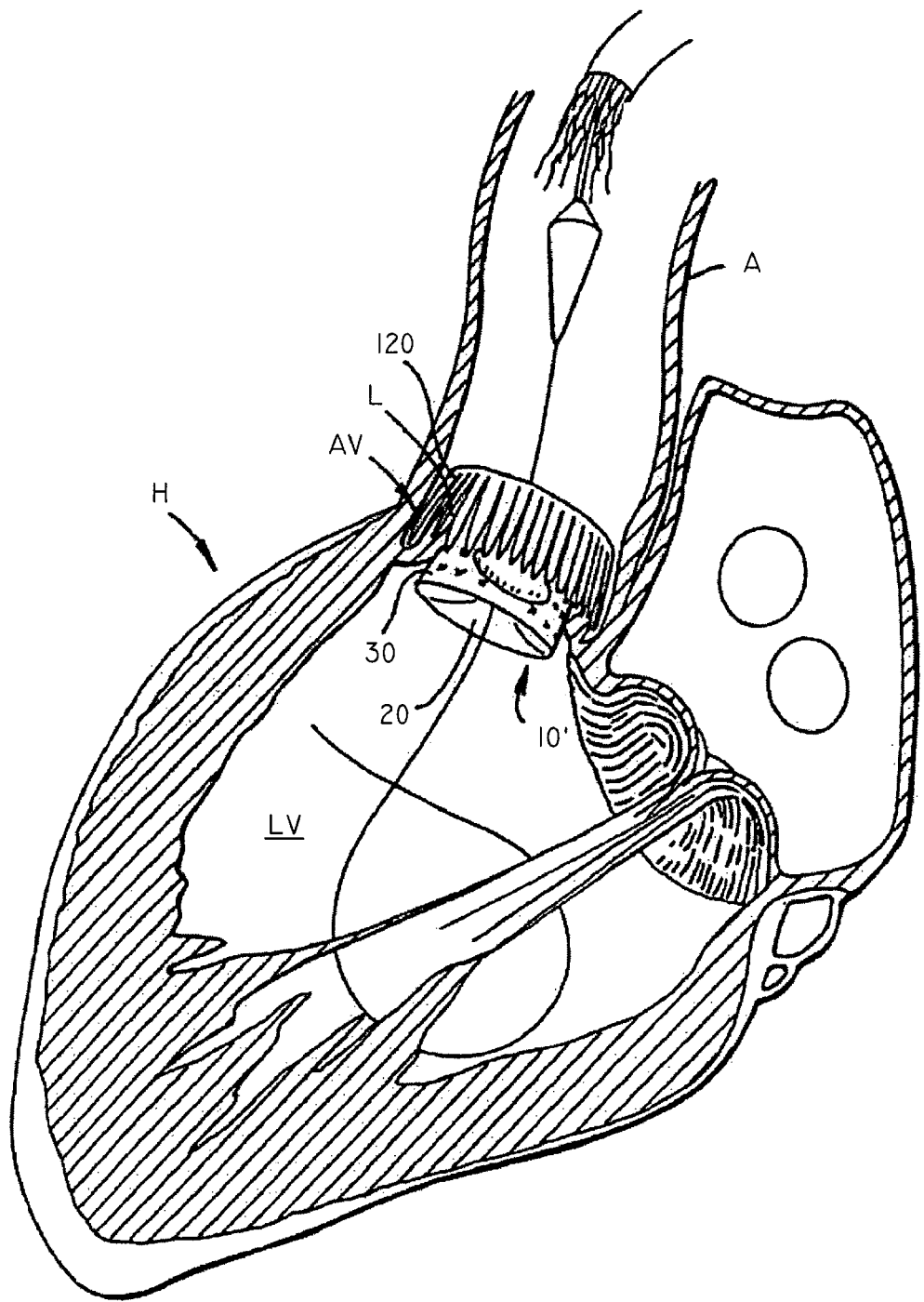
FIG. 7 illustrates a deployed anchor with leaflet engagement elements on the proximal end of the anchor.

Active expansion, e.g., foreshortening, may be imposed upon anchor 30 while elements 120 are disposed proximal of the leaflets, as is illustrated in FIG. 6D. Active foreshortening can be accomplished by actuating distal anchor actuation elements (e.g., wires 50) and/or proximal anchor actuation elements (e.g., tubes 60). Upon positive registration of elements 120 against leaflets L, elements 120 preclude further distal migration of apparatus 10 during additional foreshortening, thereby reducing a risk of improperly positioning the apparatus. FIG. 6E details engagement of elements 120 against the native leaflets.

Figure 6F:
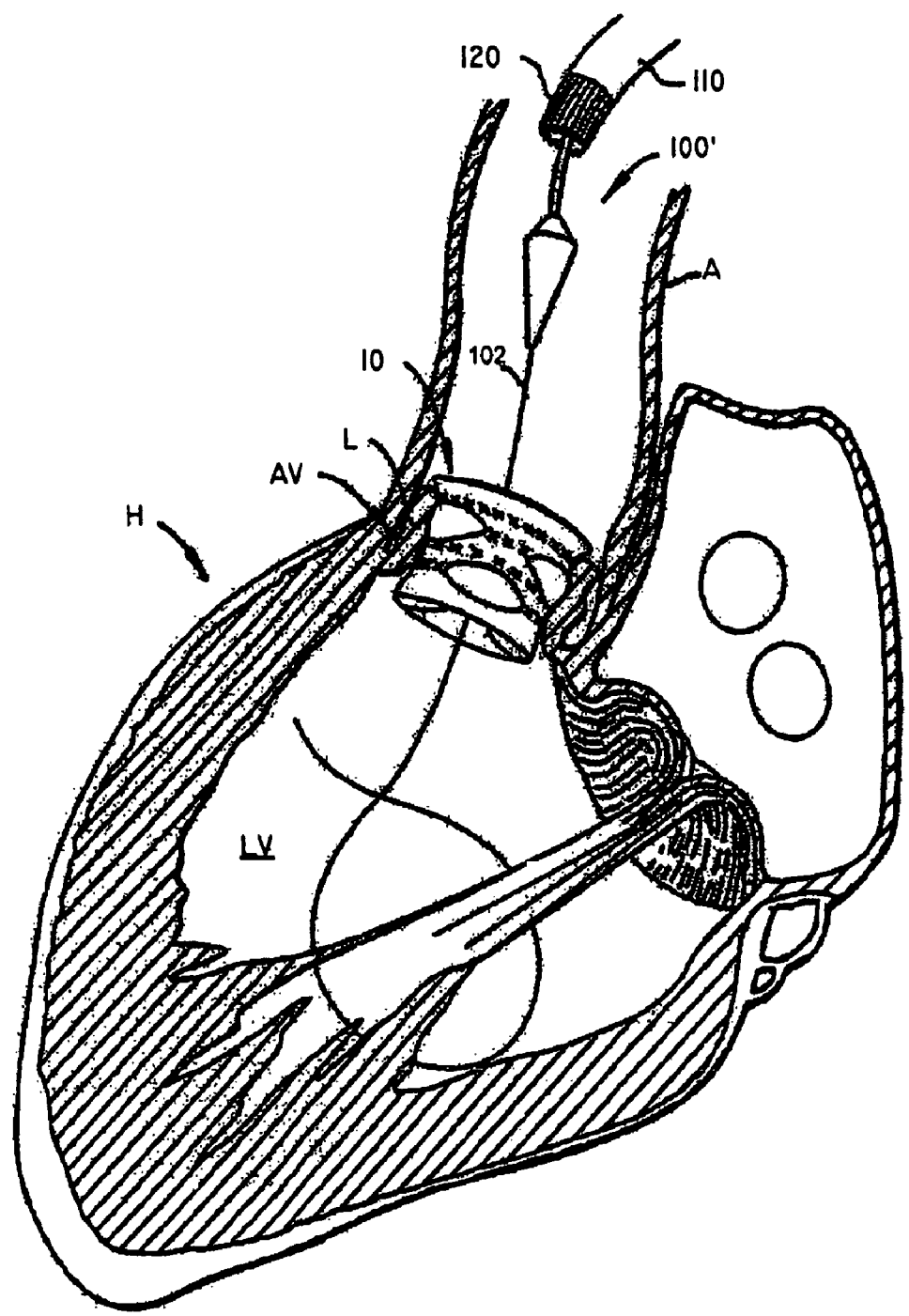

As seen in FIG. 6F, once apparatus 10 is fully deployed, anchor 30 may be locked (reversibly or irreversibly) via lock 40. Subsequently, structure 61A, leaflet engagement elements 120, wires 50 and/or tubes 60 may be decoupled from the apparatus, and delivery system 100' may be removed from the patient, thereby completing the procedure.

FIG. 7 illustrates an alternative embodiment of the apparatus of FIGS. 6A-F described above, wherein leaflet engagement elements 120 are coupled to anchor 30 of apparatus 10' rather than to delivery system 100. In the embodiment illustrated in FIG. 7, leaflet engagement elements 120 remain implanted near the patient's native heart valve after the deployment of apparatus 10' and removal of delivery system 100. Leaflets L may be sandwiched between the proximal region of anchor 30 and leaflet engagement elements 120 in the fully deployed configuration. In this manner, elements 120 positively register apparatus 10' relative to the leaflets L and preclude distal migration of the apparatus over time.

Figure 8A:
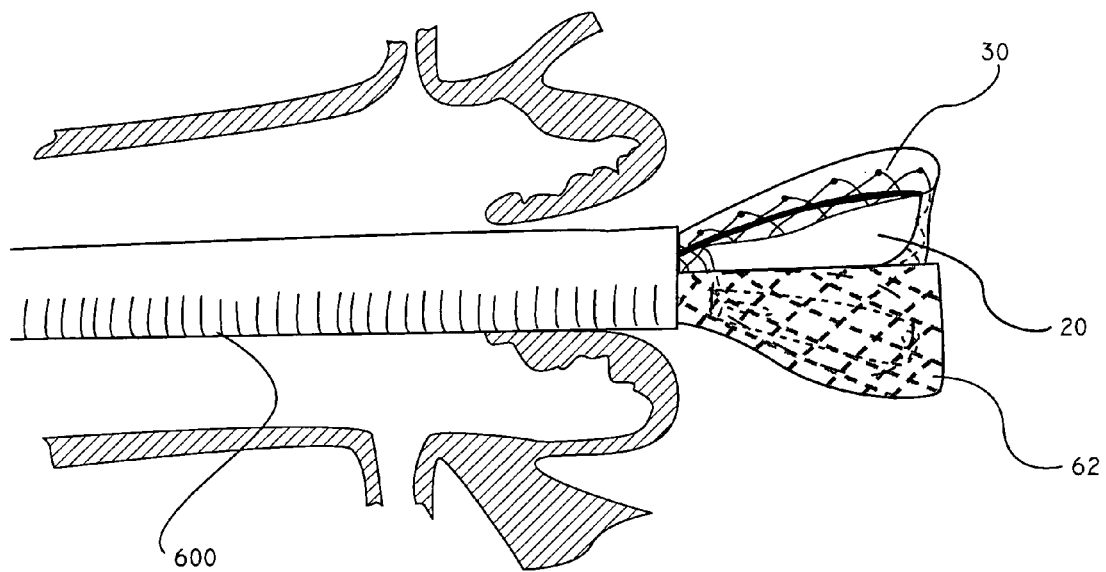
FIGS. 8A-8C illustrate deployment of an anchor with anchor registration or leaflet engagement elements and a seal.
Figure 8B:
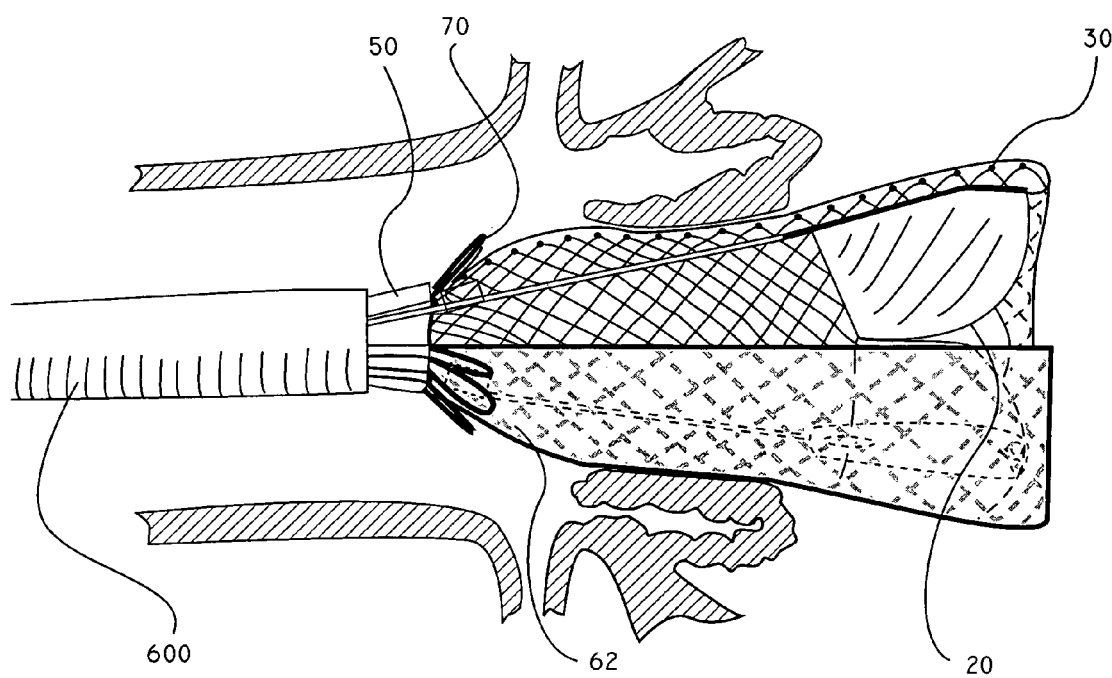
Figure 8C:
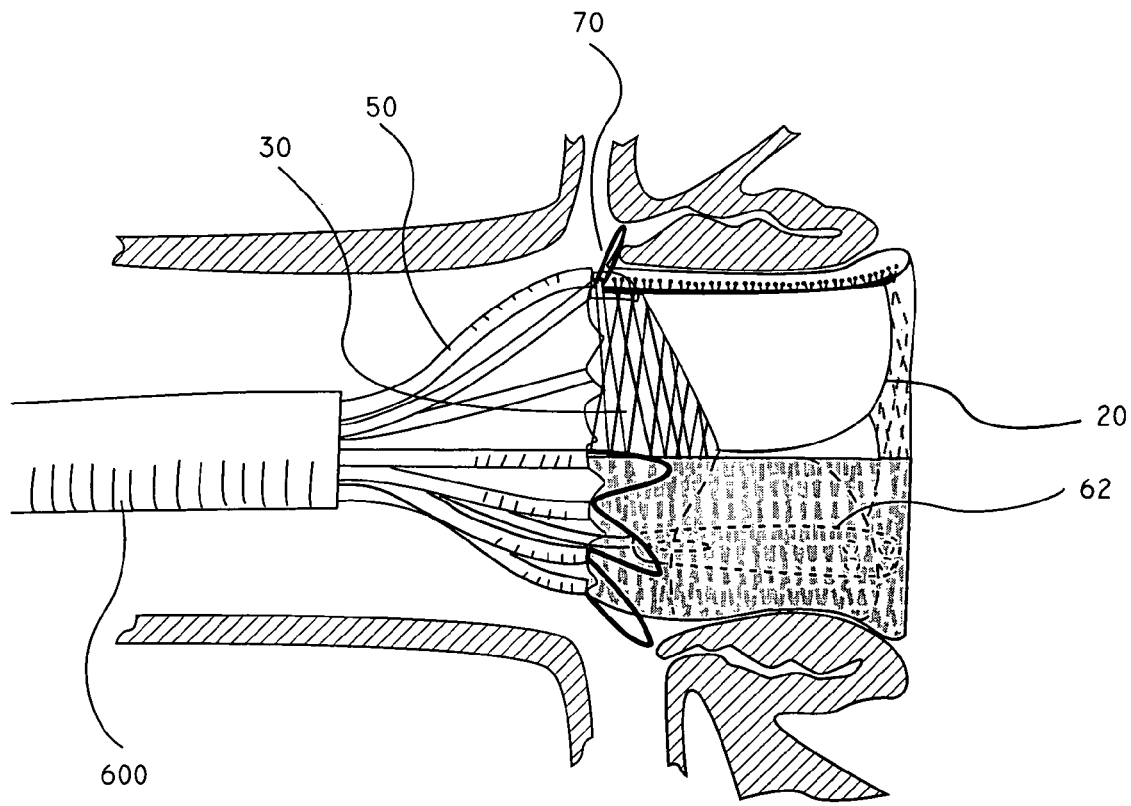

FIGS. 8A-8C illustrate another embodiment for endovascularly delivering an apparatus of the present invention. In FIG. 8A, a catheter 600 is delivered percutaneously in a retrograde fashion to the aortic valve. The catheter passes through the native aortic valve before an operator actuates the unsheathing of the anchor/valve apparatus. As the sheathing catheter is pulled proximally out of the native valve, anchor 30 and replacement valve 20 become unsheathed. Immediately the portion of the unsheathed anchor 30 dynamically self-expands to its "at-rest" position, and replacement valve 20 within the anchor regains an uncollapsed structure, allowing it to begin to function. In preferred embodiments in its "at-rest" position, anchor 30 presses against the native leaflets limiting blood from flowing in between the anchor and leaflet. Also, in preferred embodiments, anchor 30 portions relatively adjacent to the valve are externally covered by a seal 62, more preferably the entire exterior contour of anchor 30 excluding the leaflet engagement elements is externally covered by a seal, or more preferably the entire contour of anchor 30 including the external face of the leaflet engagement elements is externally covered by a seal. A seal can be composed of any material that prevents or limits the flow of blood through the anchor. In preferred embodiments, a seal is composed of a thin, elastic polymer or any other type of fabric. The seal can be attached to the anchor and, in some embodiments, to the distal end of the valve, by any means known in the art. In preferred embodiments, a seal is attached to the anchor by suturing.

In FIG. 8B, as the catheter is further pulled proximally, the proximal end of anchor 30 and anchor actuation elements or fingers 50 are unsheathed. In this embodiment, it is possible to visualize that the seal covers the entire contour of the anchor including the external face of the leaflet engagement element(s) 70. As soon as the proximal end of the anchor is exposed, it also dynamically expands. Furthermore, when fingers 50 become exposed, replacement valve 20 begins to function, permitting blood to flow through replacement valve 20, between fingers 50 and around the catheter 600. This also permits blood to flow into the coronary ostias. In other embodiments where the seal does not cover the proximal end of the anchor, the replacement valve can begin to function as soon as the unsealed portion of the anchor is unsheathed. This causes the leaflet engagement element(s) 70 to radially expand to their heat set position and engage with the native heart leaflets.

Next, as seen in FIG. 8C, as the apparatus is actively foreshortened using proximal actuators (e.g., fingers) and/or distal actuators (not shown), the leaflet engagement elements positively register with the native valve leaflets. Foreshortening can cause seal 62 to bunch up and create pleats. These pleats can then fill pockets, thereby improving the paravalvular seal. In embodiments in which the leaflet engagement elements are covered with a seal, at least a portion of the seal is also positioned between the native valve leaflets and the aortic wall. Once the anchor is fully compressed within the aortic valve, the anchor is locked, the proximal and distal actuators are disengaged, and the seal is adapted to further limit blood flow around the replacement valve. The catheter is subsequently withdrawn, leaving behind valve 20, seal 62 and anchor 70. When fully deployed, the anchor is substantially distal to the coronary ostia of the patient, such that it will not interfere with blood flow through the ostia.

Figure 9A:
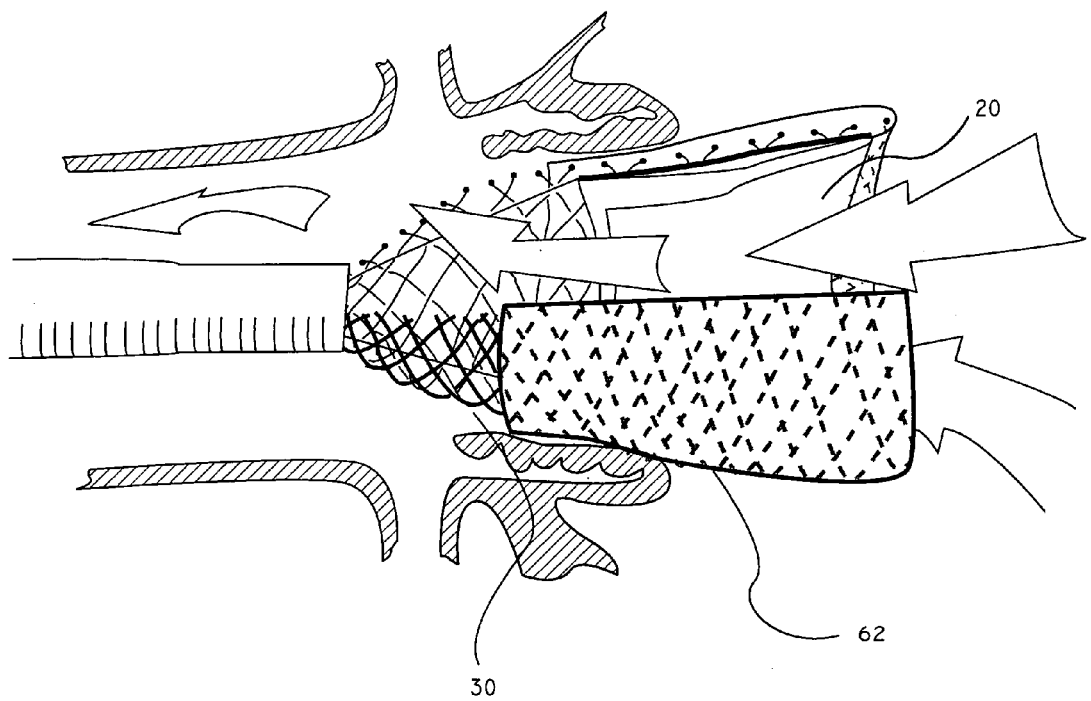
FIGS. 9A-9B illustrate an embodiment of the apparatus with a seal that does not reach the proximal end of the anchor during both systole and diastole.
Figure 9B:
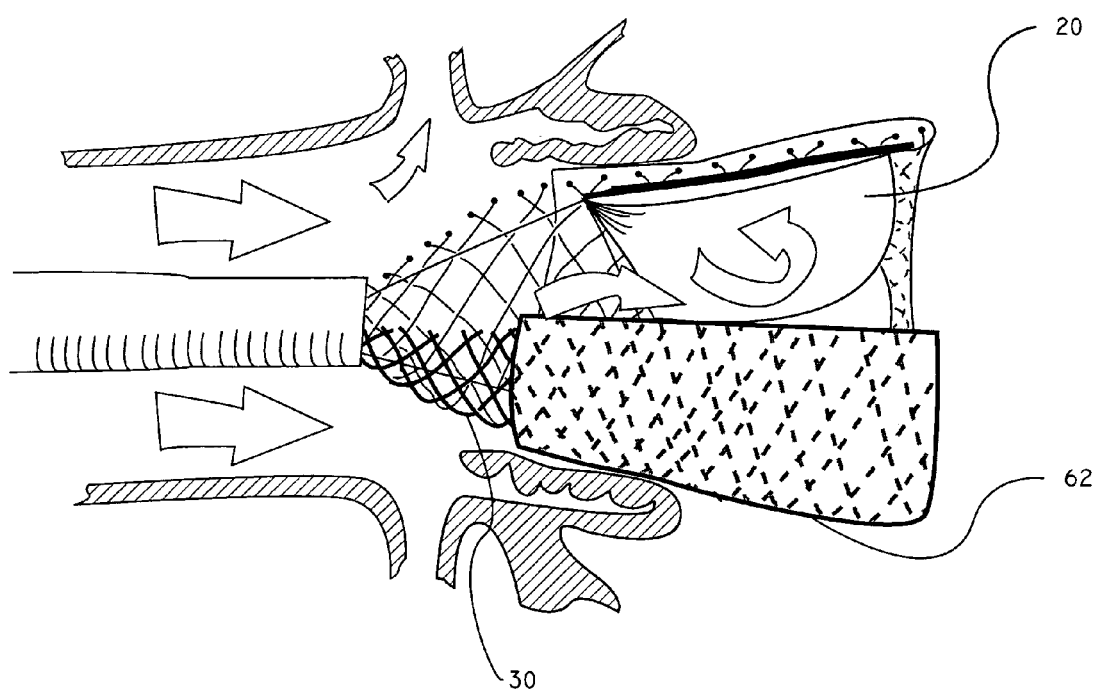

FIGS. 9A-9B illustrate an embodiment wherein only a distal portion of anchor 30 is covered by seal 62, and wherein anchor 30 is only partially deployed since the blood can escape through the proximal end of the anchor braid. As anchor 30 in this embodiment is unsheathed, it presses against the native valve leaflets. At this point replacement valve 20 is functional even though anchor 30 is not fully deployed, since blood can escape through the proximal end of the anchor braid. This allows blood to flow through replacement valve 20 and out of holes in the distal end of anchor 30 during systole (FIG. 9A) while preventing backflow during diastole (FIG. 9B).

Figure 10A:
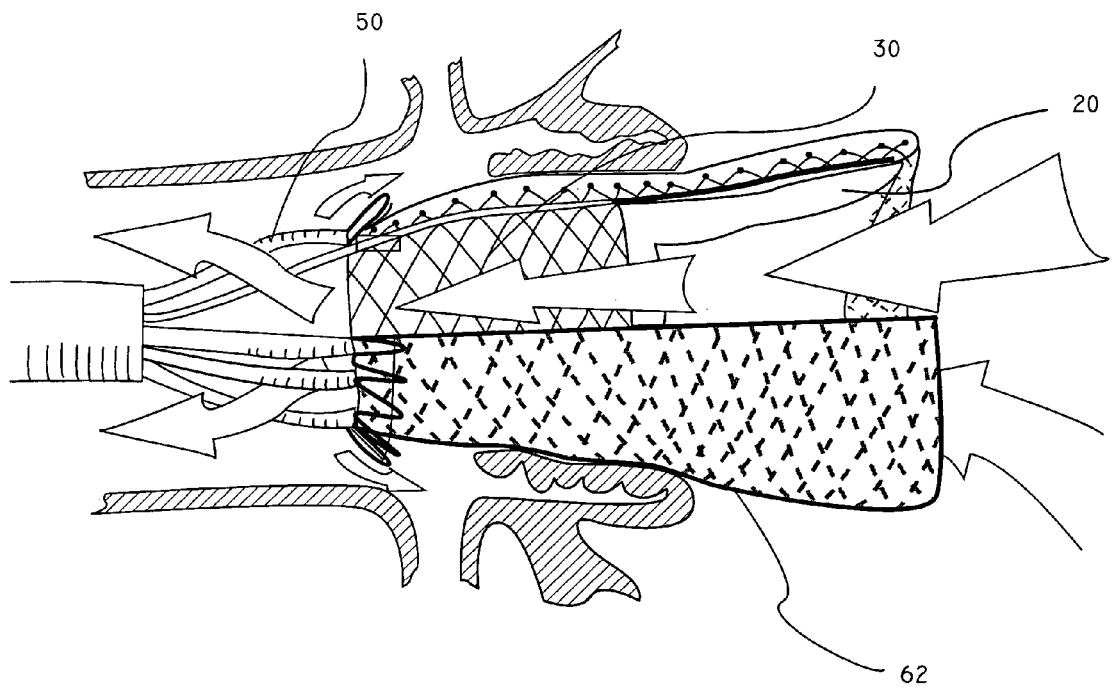
FIGS. 10A-10B illustrate an embodiment of the apparatus with a seal that reaches the proximal end of the anchor during both systole and diastole.
Figure 10B:
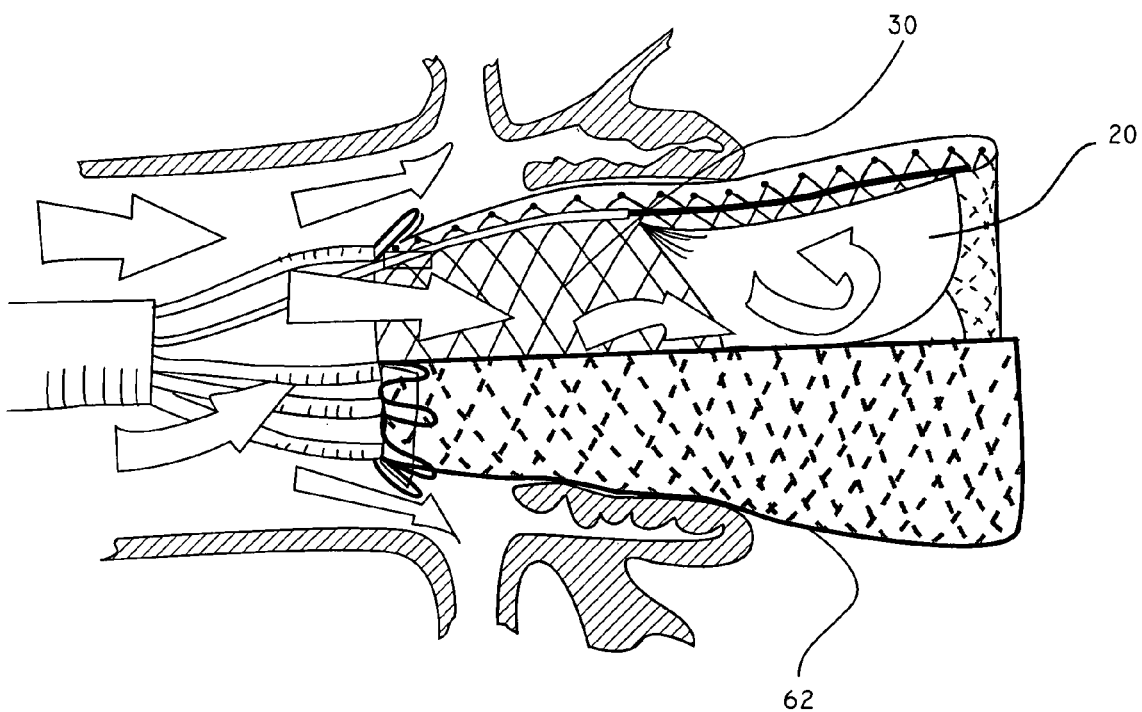

FIGS. 10A-10B illustrate a similar embodiment wherein seal 62 around anchor 30 surrounds the entire contour of anchor 30. In this embodiment, valve 20 does not become functional until both anchor 30 and a portion of fingers 50 are unsheathed. As soon as a portion of fingers 50 is unsheathed, replacement valve 20 is fully functional. This allows blood to flow through replacement valve 20 and anchor 30, out of fingers 50, and around catheter 600 into the aorta and coronary ostias during systole. Similarly, during diastole, replacement valve 20 closes preventing blood backflow from entering the chamber.

In any of the embodiments herein the anchor is preferably a self-expanding anchor braid. Anchor braids of the present invention can be made from one or more wires, more preferably 2-20 wires, more preferably 3-15 wires, or more preferably 4-10 wires. Moreover, the density of the braid can be modified by various forms of weave used.

FIGS. 11A-11D illustrate various anchor braid embodiments contemplated by the present invention.

FIG. 11A illustrates two groups of cells or two braids interwoven in the center. The top group of cells forms a more open weave than the bottom group of cells, which forms a denser weave.

FIG. 11B illustrates another embodiment of an anchor braid having three groups of cells. The top and bottom (proximal and distal) edges of the anchor braid have denser cells than the central portion of the anchor. Also, the edges of the anchor are woven from a thinner filament than the central portion.

Figure 11C:
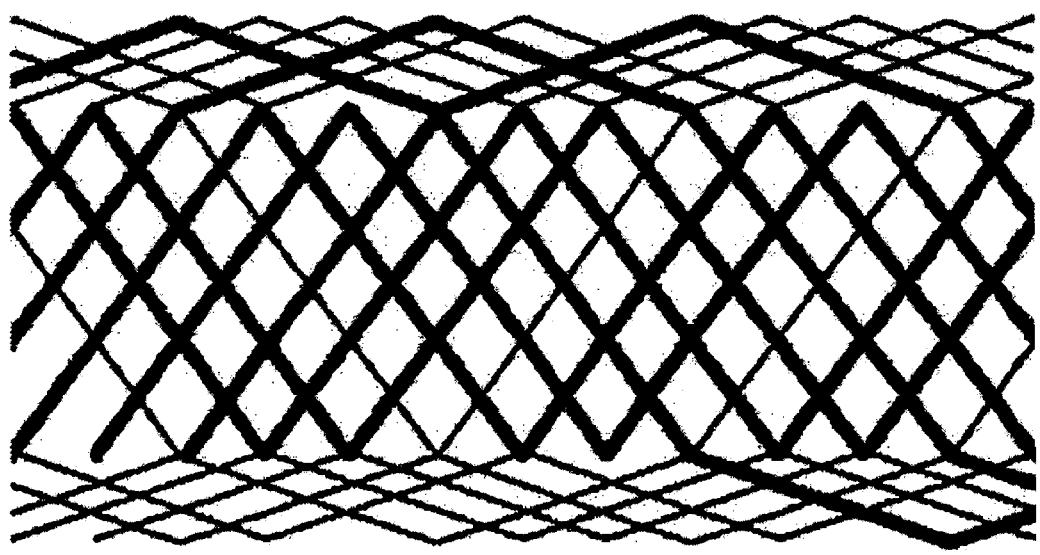

In another embodiment illustrated by FIG. 11C, all three sections of an anchor valve are woven by more than one wire. The wires of each section are made of a different material and/or thickness. Wires at the sectional boundaries may or may not interconnect with wires from a different section. Each of the sections of the braid anchor may be composed of a different number of wires.

Figure 11D:
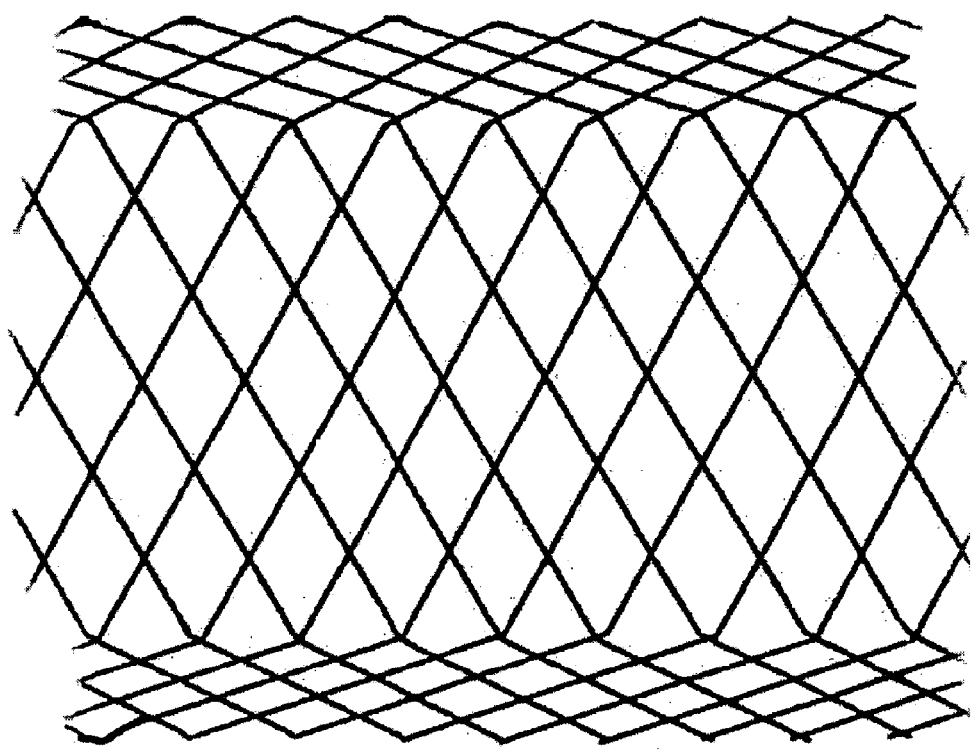

FIG. 11D illustrates another embodiment of a braided anchor having three sections. In this embodiment, all sections are composed of a single wire. The proximal and distal sections/edges of the braided anchor have the same pitch. The central region of the braided anchor has a different pitch than the edge sections.

FIGS. 12A-12E illustrate side views of braided anchors having more than one braid pitch. Varying pitch within the anchor allows localized variations in foreshortening across the anchor, as greater foreshortening is achieved by higher pitch of the braid. Moreover, the localized foreshortening features allow for the design of a braid which incorporates various diameters depending upon the amount of foreshortening. (The greater the foreshortening, the greater the diameter increase upon deployment.)

Figure 12A:
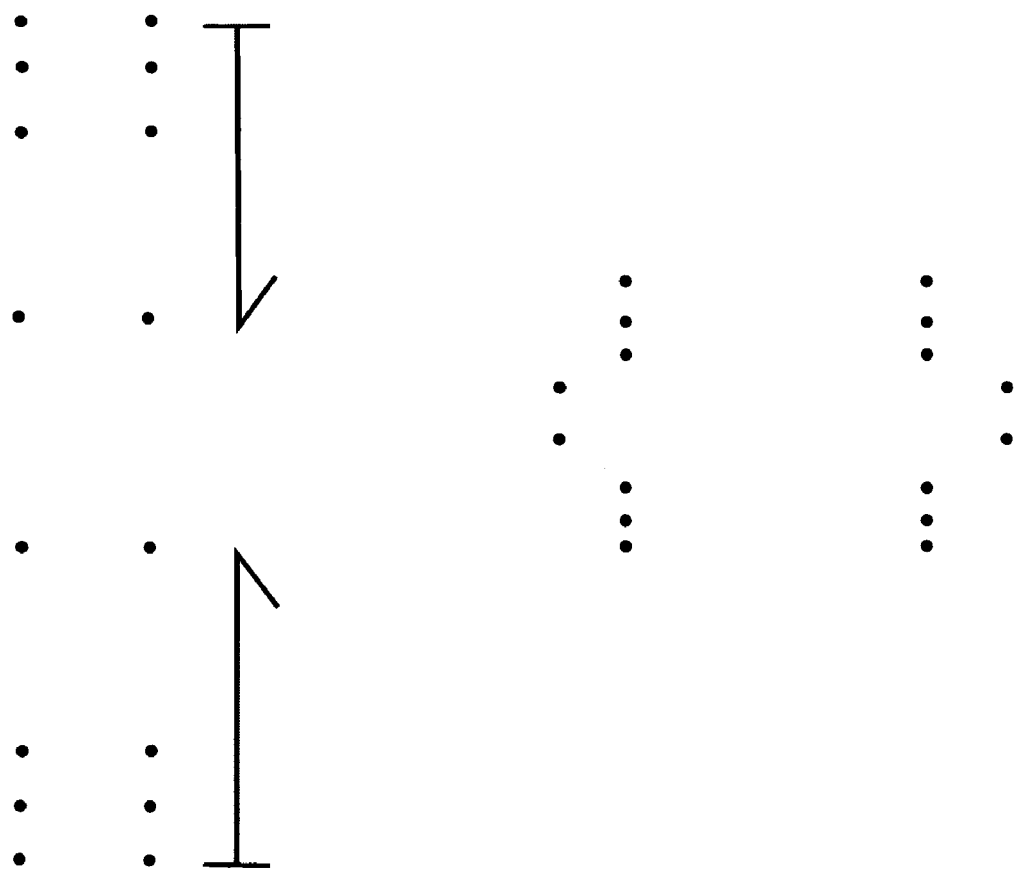
FIGS. 12A-12E are schematic side views of a deployment process for an anchor braid.

FIG. 12A, is a side view representation of the braided anchor of FIG. 11D. On the left side of the figure, the expanded anchor is illustrated having a denser weave (shorter pitch) at the distal and proximal ends; hence the dots are located closer to each other. The middle section of the anchor is composed of a looser weave that is generated by a higher pitch braid and is represented by dots that are farther away from each other. On the right side of the figure, the braided anchor is foreshortened and the dots are collapsed closer to each other. In this case, the central portion of the anchor foreshortened more than the proximal and distal edges.

Figure 12B:

FIG. 12B illustrates a side view of a foreshortened braided anchor that is created by low pitch at the edges and high pitch in the middle.

Figure 12C:

FIG. 12C illustrates a side view of a foreshortened braided anchor that is created by high pitch edges and low pitch middle section.

Figure 12D:

FIG. 12D illustrates a side view of a foreshortened braided anchor that includes a sealing feature or space filling feature at both ends. This type of anchor can be created by a high pitch braid at edges, low pitch braid in the middle and heat setting the edges to curl upon unsheathing. These end features can be useful in facilitating anchoring by functioning as a locator and/or sealing. In one embodiment, the curled ends of the anchor in FIG. 12D can be used as tissue engagement elements.

Figure 12E:

FIG. 12E illustrates a side view of a foreshortened braided anchor that is associated with an everting valve or locational/engagement/grasping features. In preferred embodiments, the middle section of the anchor may be composed of thicker wire(s) than edge section(s). For example, an everting feature at the proximal end can function as a leaflet engagement element as disclosed herein.

FIGS. 13A-13E illustrate an example of the process of deploying an anchor, such as the one illustrated in FIG. 12B above.

FIG. 13A illustrates a braided anchor 30 in its expanded or elongated configuration. The anchor is composed of three sections. The distal and proximal sections of the anchor are made of a fine weave, low pitch braid and the middle section of the anchor is made of a thicker thread and higher pitch braid. The distal and proximal section are preferably heat set to roll upon unsheathing, though some rolling may occur simply from active foreshortening of the fine weave braid. In preferred embodiments, the filaments of the fine weave braid are less than 0.01 cm, or more preferably less than 0.005 cm in thickness. On the other hand, thicker filaments of the middle section-are preferably 0.01 cm or greater in thickness or more preferably 0.015 cm or greater in thickness. Posts 32 are coupled to the middle section of the anchor. For deployment, tubes (or fingers) 106 are coupled to the anchor's middle section.

FIG. 13B illustrates an anchor during the process of deployment after the anchor is unsheathed. The anchor is pushed distally by tubes and pulled proximally by wires and begins foreshortening. In some embodiments, the distal section rolls up and can act as a locator, assisting the operator in locating the aortic valve or engaging the valve annulus, or as a seal preventing leakage. In some embodiments, the proximal section may roll down and be used as a leaflet engagement element to prevent distal migration or as a proximal seal.

In FIG. 13C, the device may be configured such that the middle section of the valve may form an hour glass shape or a round shape. The tubes may subsequently be removed as described before.

FIG. 13D is another illustration of the braided anchor in its elongated configuration.

FIG. 13E is another illustration of the braided anchor in its foreshortened configuration.

Figure 14A:
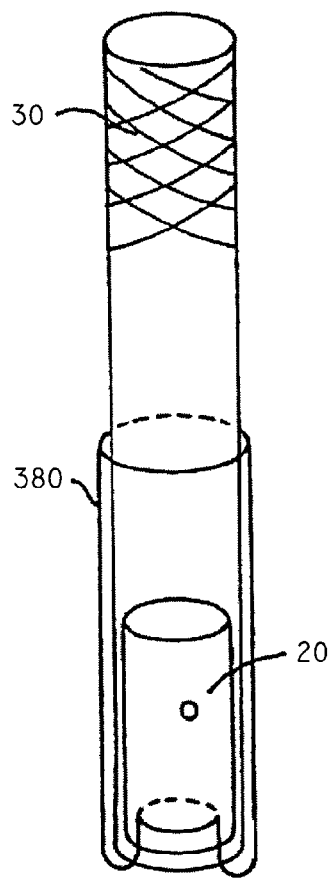
FIGS. 14A-14C illustrate an embodiment of a replacement heart valve and anchor in the undeployed and deployed configurations.
Figure 14B:
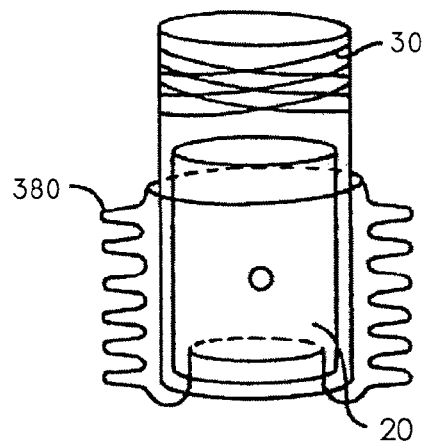
Figure 14C:
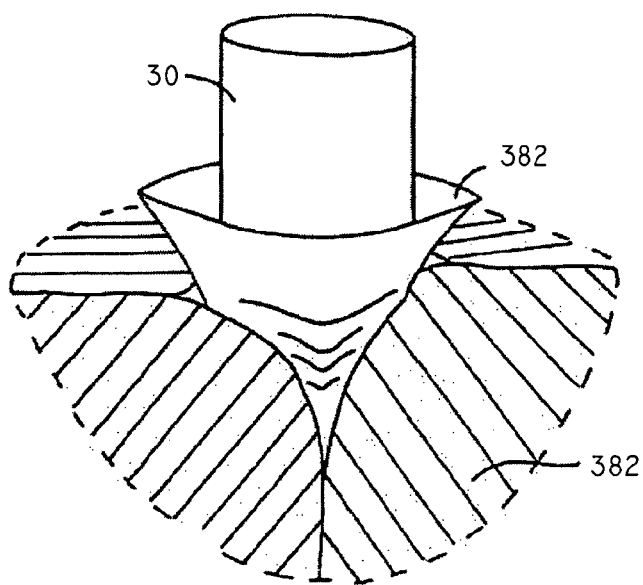

FIGS. 14A-14C illustrate the process of forming a pleated seal around a replacement valve to prevent leakage. FIG. 14A illustrates a fabric seal 380 prior to deployment and foreshortening of the anchor/valve apparatus. In FIG. 14A, the fabric seal 380 extends from the distal end of valve 20 proximally over anchor 30 during delivery. During deployment, as illustrated in FIG. 14B, anchor 30 foreshortens, and the fabric seal 380 bunches up to create fabric flaps and pockets that extend into spaces formed by the native valve leaflets 382. The bunched up fabric or pleats occur, in particular, when the pockets are filled with blood in response to backflow blood pressure. The pleating can create a seal around the replacement valve. FIG. 14C illustrates anchor 30, surrounded by fabric seal 380 in between native valve leaflets 382. In preferred embodiments, at least a portion of a seal is captured between the leaflets and the wall of the heart when the anchor is fully deployed Referring now to FIGS. 15 and 16, a replacement heart valve and anchor having engagement elements configured to grasp tissue in the vicinity of a patient's heart valve is described. The grasping engagement elements are configured to rotate about the anchor during active expansion of the anchor. Such rotation may be used to grasp the tissue, e.g., to grasp leaflets of the patient's native heart valve. The grasping elements preferably grasp tissue atraumatically.

Anchor 30 comprises grasping elements 80. The grasping elements may comprise, for example, heat-set end turns Tu of a braid from which the anchor is fabricated, a special weave of the braid, or multiple wires attached to one another by crimping, welding or other means. The grasping elements may be integral with anchor 30 or may be attached to the anchor, for example, via interweaving, crimping, welding, soldering, wire wrapping, or other suitable attachment means. Grasping elements 80 may have a different cross-sectional profile than that of the material from which the body of anchor 30 is fabricated, e.g., from that of the wires forming the braid of anchor 30. Additionally or alternatively, the grasping elements may be fabricated of different materials than those from which the anchor is fabricated and/or from which other grasping elements are fabricated.

In FIG. 15, grasping elements 80 illustratively extend from a proximal region of the anchor, e.g., for atraumatic grasping of tissue of the patient's native valve leaflets. Such grasping of the valve leaflets may facilitate proper positioning of the anchor distal of the coronary ostia, and also might resist distal movement of the anchor. Grasping elements may additionally or alternatively extend from a distal region of the anchor, e.g., for atraumatic grasping of the annulus of the patient's heart valve. Such grasping of the annulus may facilitate positioning proximal of the mitral apparatus, and also might resist proximal movement of the anchor.

Figure 15A:
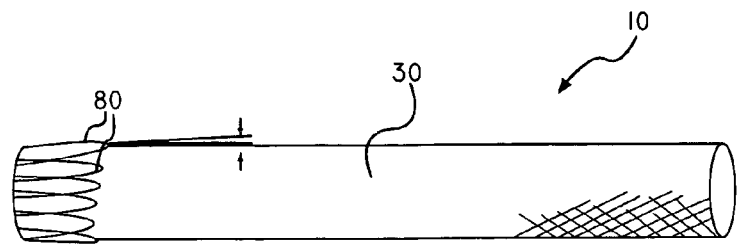
FIGS. 15A-15D illustrate an embodiment of a replacement heart valve and anchor having tissue grasping elements that rotate about the anchor during active expansion of the anchor.
Figure 15B:
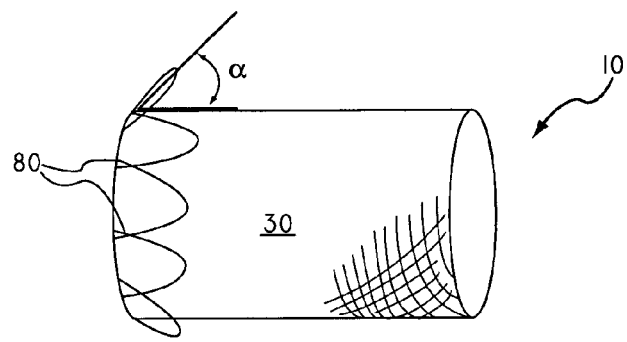
Figure 15C:
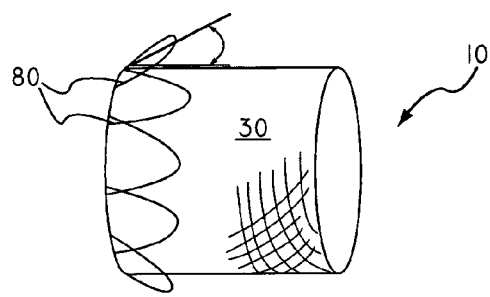
Figure 15D:
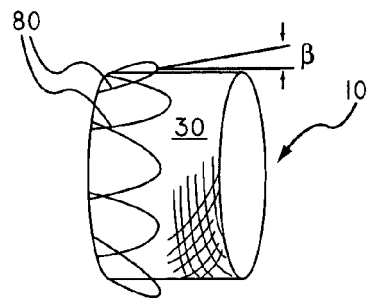

Anchor 30 comprises a self-expanding anchor having a delivery configuration, as seen in FIG. 15A; an at-rest configuration, as seen in FIG. 15B; and a deployed configuration, as seen in FIG. 15D. The anchor may, for example, self-expand from the delivery configuration to the at-rest configuration after deployment from a delivery sheath. The anchor then may be actively expanded, e.g., foreshortened, to the deployed configuration of FIG. 15D, in which configuration it may, for example, be locked using, e.g., one of the lock mechanisms described above. FIG. 15C illustrates the anchor during active expansion and during transition from the at-rest configuration to the deployed configuration. Grasping elements 80 may move radially relative to one another during expansion of the anchor. For example, in FIG. 15, the grasping elements move radially apart during self-expansion of the anchor to the at-rest configuration, then move radially closer together during active expansion to the deployed configuration.

As seen in FIG. 15A, grasping elements 80 are positioned substantially parallel with anchor 30 in the delivery configuration, e.g., the grasping elements lie substantially flat against the anchor during delivery. The grasping elements may be constrained to lie flat by an exterior constraint, such as the delivery sheath. As seen in FIG. 15B, grasping elements 80 form a first angle α with the anchor in the at-rest configuration. As seen in FIG. 15C, as the anchor expands to the deployed configuration, the grasping elements 80 rotate about anchor 30, such that the angle α changes. In the fully deployed configuration of FIG. 15D, the grasping elements form a second angle β with the anchor. If a lock is provided with the anchor, locking the anchor in its deployed configuration helps maintain the anchor's grasp of the tissue.

The first angle α illustratively is larger than the second angle β, such that the grasping elements rotate inward toward the body of anchor 30 during active anchor expansion from the at-rest configuration to the deployed configuration. The grasping elements may grasp tissue, such as the patient's valve leaflets, between the body of the anchor and the grasping elements during such rotation of the grasping elements. As seen in FIG. 15D, the second angle β may, for example, approximate zero when no tissue is grasped or captured between the grasping element and the anchor. In alternative embodiments of grasping elements 80, the second angle β may be larger than the first angle α, such that the grasping elements rotate outward and away from the body of the anchor for grasping tissue during active anchor expansion. In still further alternative embodiments, the second angle β may be substantially equal to the first angle α, such that the grasping elements do not rotate, or rotate only minimally, during active expansion of the anchor.

Figure 16:
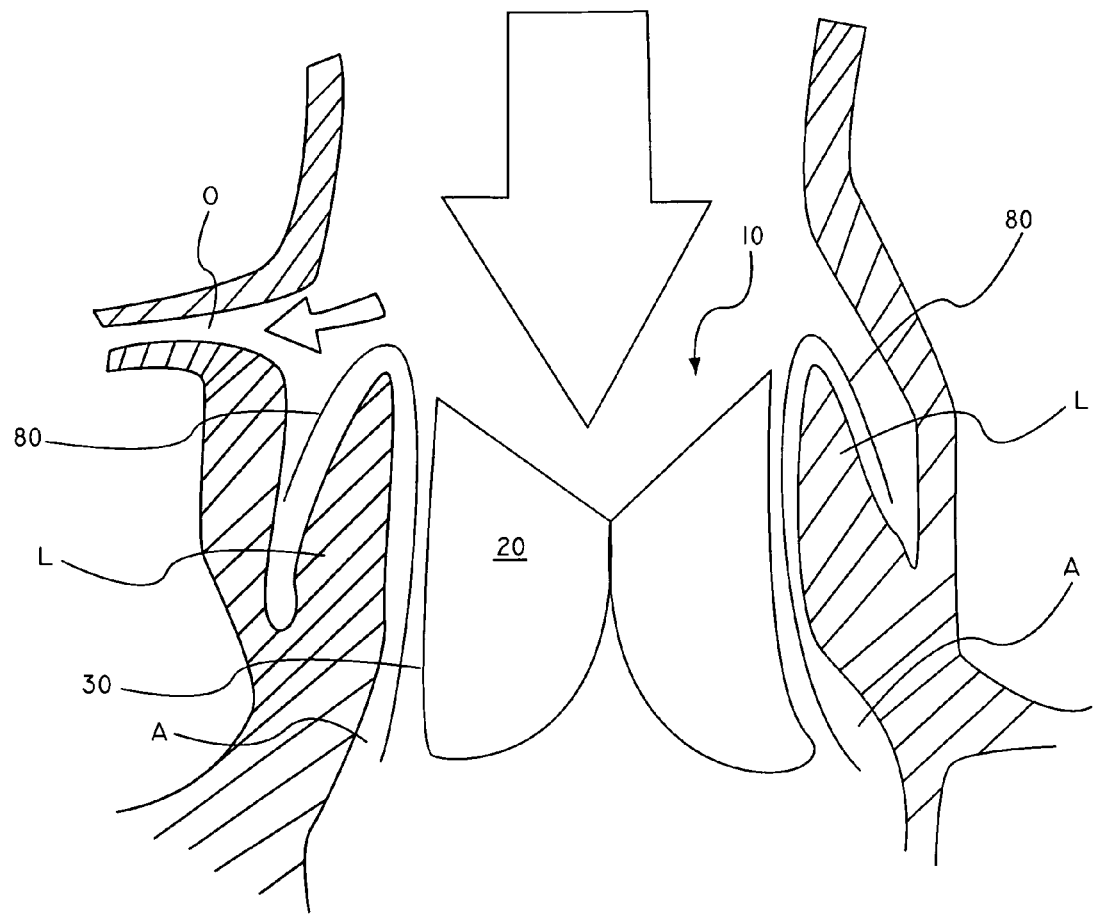
FIG. 16 is a cross-sectional view illustrating the apparatus of FIG. 15 deployed across a patient's native valve.

FIG. 16 shows anchor 30 and replacement valve 20 deployed across a patient's native valve. Grasping elements 80 rotate inward towards the body of anchor 30 during expansion of the anchor, thereby grasping leaflets L of the patient's aortic valve and pulling the leaflets toward the anchor, e.g., during diastole. This grasping of the leaflets secures the apparatus against the native valve, thereby resisting distal migration of the apparatus and/or leakage. Furthermore, grasping elements 80 ensure that apparatus 10 is disposed distal of coronary ostia O and extends distal of the leaflets to valve annulus A.

With reference now to FIG. 17, anchor 30 may comprise any of a variety of grasping elements 80. In FIG. 17A, the anchor illustratively comprises five separate grasping elements to grasp the leaflets around the entire circumference of the valve. The anchor may, for example, comprise 3-6 grasping elements for grasping the leaflets. Alternatively, the anchor may comprise more than six grasping elements, as in FIG. 17B. Providing additional grasping elements may facilitate grasping of the commissures of the leaflets. Furthermore, providing multiple grasping elements may distribute forces applied to the tissue amongst the grasping elements, thereby reducing a risk of misalignment of the anchor and/or replacement valve. As with the earlier embodiments, this embodiment may also be provided with a lock mechanism to maintain expansion of the anchor and grasping of the tissue.

Figure 18A:
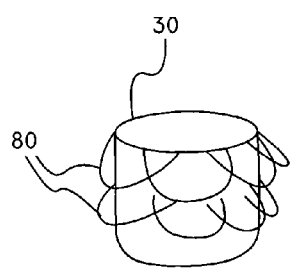
FIGS. 18A-18C illustrate additional variations of the grasping elements.

With reference to FIG. 18, in addition to altering the number of grasping elements, the location and/or orientation of the grasping elements also may be altered. FIG. 18 show variations of anchor 30 in the deployed (and possibly locked) configuration. In FIG. 18A, the anchor comprises two circumferential sets of grasping elements 80 spaced from one another along the length of the anchor. In one variation described hereinbelow with respect to FIG. 19, the grasping elements of FIG. 18A provide an outwardly-directed force such that the proximal set of grasping elements may, for example, grasp wall tissue, while the more distal set may grasp the interior of the patient's valve leaflets and press the leaflets against the wall.

Figure 18B:
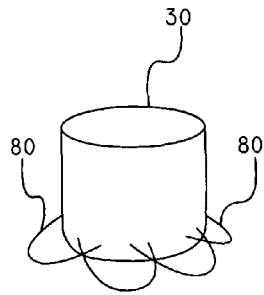
Figure 18C:
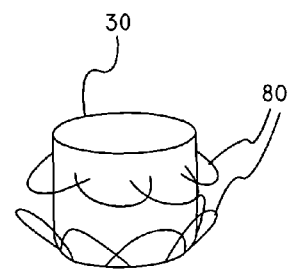

In FIG. 18B, the grasping elements extend from the distal region of anchor 30, for example, to grasp the annulus of the patient's valve. In FIG. 18C, the anchor comprises a circumferential set of grasping elements that extend from the proximal region of the anchor for grasping the patient's valve leaflets, as well as a circumferential set of the grasping elements that extend from the distal region of the anchor for grasping the patient's valve annulus. The proximal grasping elements are oriented distally to facilitate grasping of the leaflets, while the distal grasping elements are oriented proximally to facilitate grasping of the annulus.

Figure 19A:
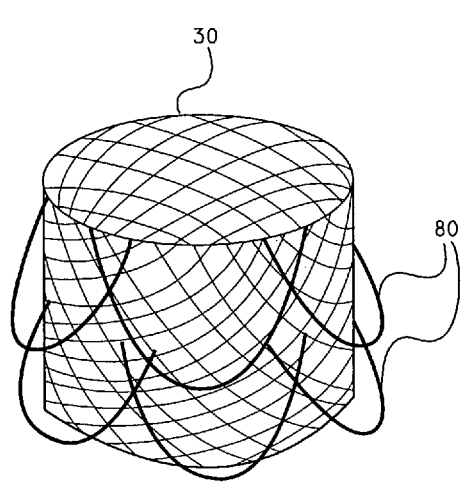
FIGS. 19A and 19B illustrate a variation of the grasping elements that applies an outwardly-directed force, which can accommodate enlargement in a patient's native valve structures over time.
Figure 19B:
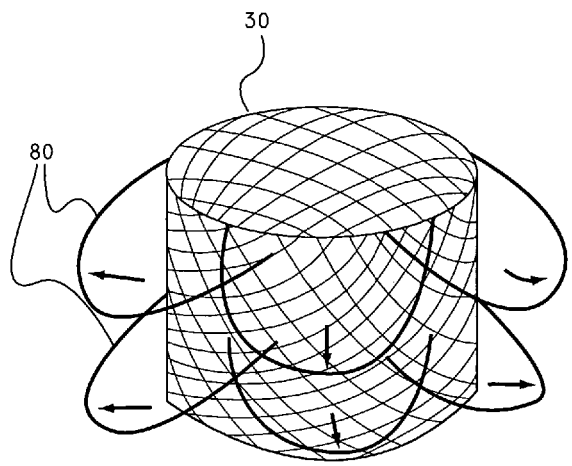

Referring now to FIG. 19, a variation of the grasping elements of FIG. 18A that can accommodate enlargement in a patient's native valve structures over time is described. In FIG. 19, grasping elements 80 apply an outwardly-directed force when anchor 30 is deployed. Anchor 30 may be deployed such that grasping elements 80 grasp tissue in the vicinity of the patient's heart valve, for example, such that the proximal grasping elements grasp wall tissue and the more distal elements grasp the interior of the valve leaflets and press them against the wall. Over time, the patient's native valve structures may expand. If the anchor is locked in the expanded configuration, it may be unable to further expand with the native structures. As seen in FIG. 19B, since the grasping elements apply an outwardly-directed force, they rotate outward relative to the anchor as the native structures expand, thereby accommodating such expansion and reducing a risk of migration of the anchor or blood leakage around the anchor.

FIG. 20 show deployment and resheathing of apparatus 10 comprising grasping elements 80. As seen in FIG. 20A, apparatus 10 having replacement valve 20 and anchor 30 with grasping elements 80 is positioned in the delivery configuration within sheath 110 of delivery system 100. Grasping elements 80 are positioned substantially parallel to, and/or lie flat against, anchor 30.

Figure 20A:
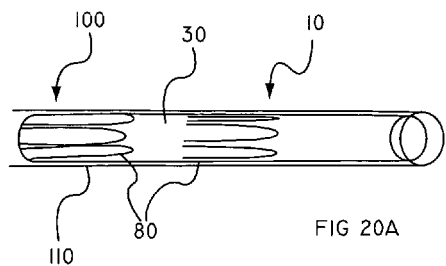
FIGS. 20A-20E illustrate deployment and resheathing of a replacement valve and anchor having grasping elements via a delivery system.
Figure 20B:
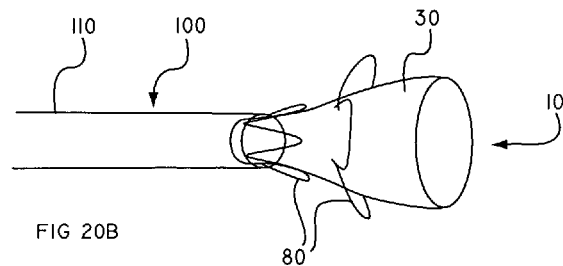
Figure 20C:
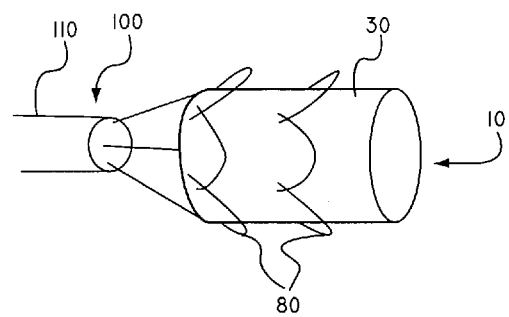
Figure 20D:
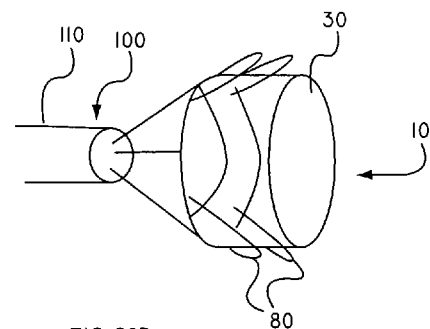

In FIG. 20B, as the sheath is retracted relative to apparatus 10, the anchor and grasping elements begin to dynamically self-expand. The grasping elements positioned along the proximal region of the anchor move laterally apart from the grasping elements positioned along the central region of the anchor as the anchor self-expands. In FIG. 20C, once the sheath has been fully retracted, the anchor assumes the at-rest configuration with the grasping elements 80 forming a first angle α with the body of the anchor. It should be understood that each grasping element 80 may form its own, potentially distinct, angle with the anchor.

Anchor actuation elements 106 then may be used in conjunction with distal control wires and other elements of delivery system 100 to actively expand the anchor (and optionally lock the anchor), as described previously. Grasping elements 80 rotate relative to anchor 30 during active expansion of the anchor and form a second angle β with the anchor in the fully deployed configuration of FIG. 20D. As with the first angle α, each grasping element 80 may form its own, potentially distinct, second angle β with the anchor. The second angle(s) β may be larger or smaller than the first angle(s) α, i.e., the grasping elements may rotate outward or inward relative to the anchor. In some embodiments, the second angle(s) β may be substantially equal to the first angle(s) α, i.e., the grasping elements may not rotate, or may rotate only minimally, during active expansion of the anchor. In FIG. 20, the grasping elements rotate inward and the proximal grasping elements move laterally closer to the more distal grasping elements during active expansion.

Figure 20E:
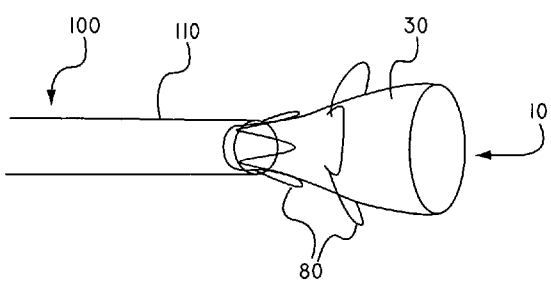

FIG. 20E illustrates that the anchor may be resheathed, e.g., within sheath 110, after deployment of the anchor. The grasping elements again lie substantially flat against the anchor during resheathing. The apparatus may be repositioned or retrieved via resheathing.

Figure 21:
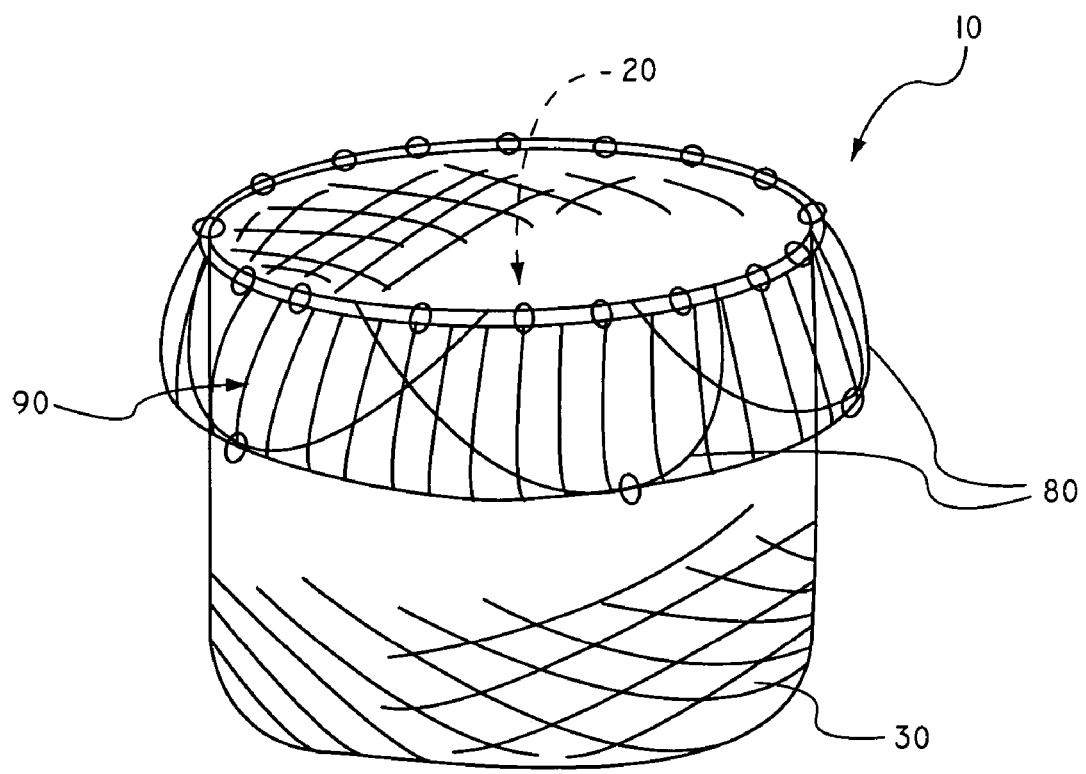
FIG. 21 illustrates a seal for use with grasping elements coupled to an anchor.

Referring now to FIG. 21, a seal for use with grasping elements 80 is described. Seal 90 of FIG. 21 only covers the grasping elements 80, such that the seal does not interfere with the primary anchoring function of anchor 30. Seal 90 illustratively covers all grasping elements 80, but alternatively may cover only a subset of the grasping elements. Furthermore, the seal may be utilized regardless of the positioning, orientation or quantity of the grasping elements. The seal may be captured between leaflets of the patient's heart valve and a wall of the patient's heart when the anchor and replacement valve are fully deployed. The seal may be adapted to reduce or prevent blood flow around the replacement valve when the anchor and replacement valve are fully deployed.

Figure 22:
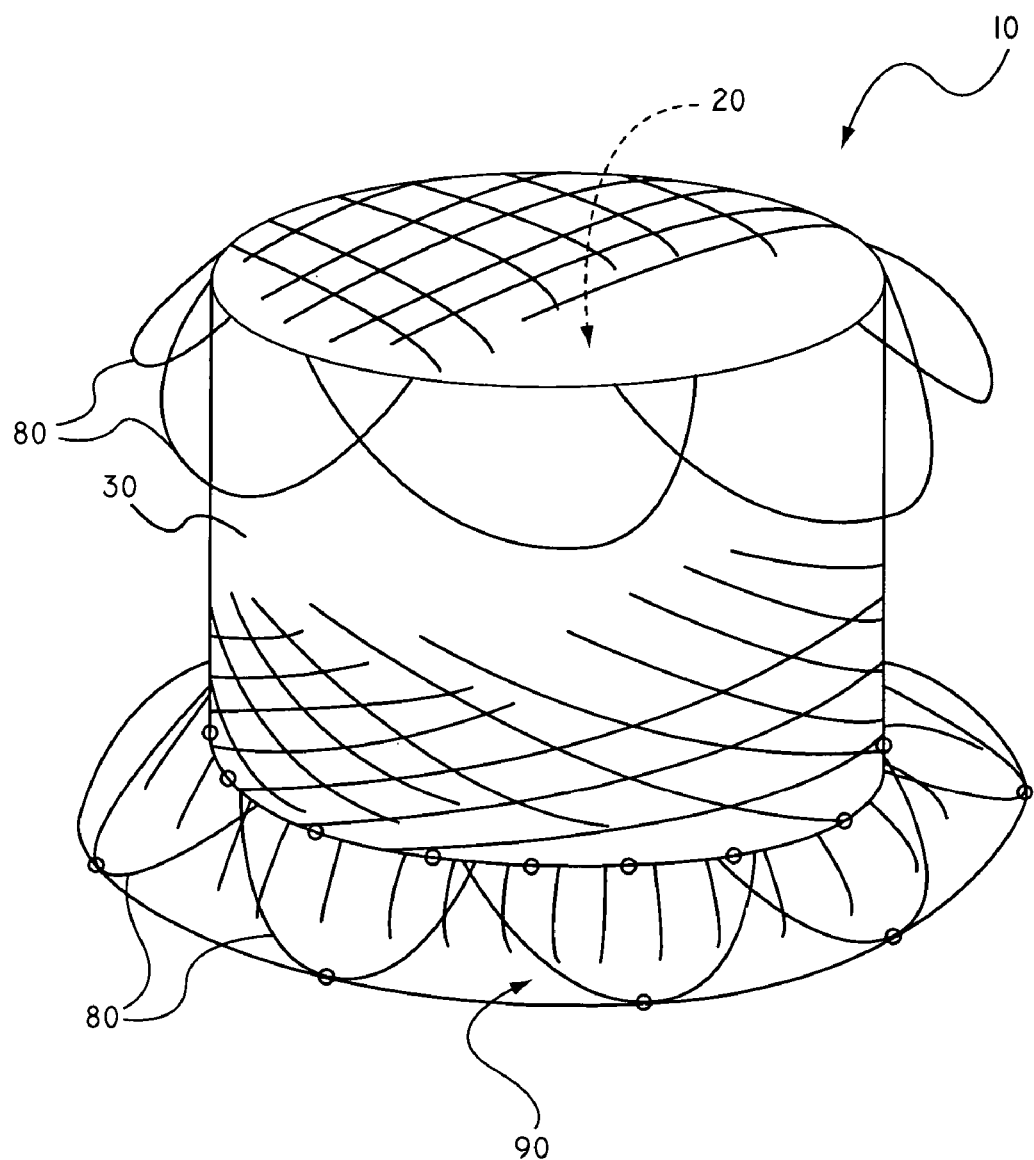
FIG. 22 illustrates an alternative embodiment of the grasping elements and seals of FIG. 21.

FIG. 22 illustrates an alternative embodiment of the grasping elements and seals of FIG. 21. In FIG. 22, anchor 30 comprises both proximal grasping elements 80 for grasping valve leaflets and distal grasping elements 80 for grasping the annulus of the patient's valve. Seal 90 illustratively is positioned only over the distal grasping elements, such that the seal is captured against an annulus of the patient's heart valve in the deployed configuration. The seal forms a distal 'skirt' that reduces or prevents blood flow around the replacement valve when the anchor and the replacement valve are fully deployed.

Figure 23:
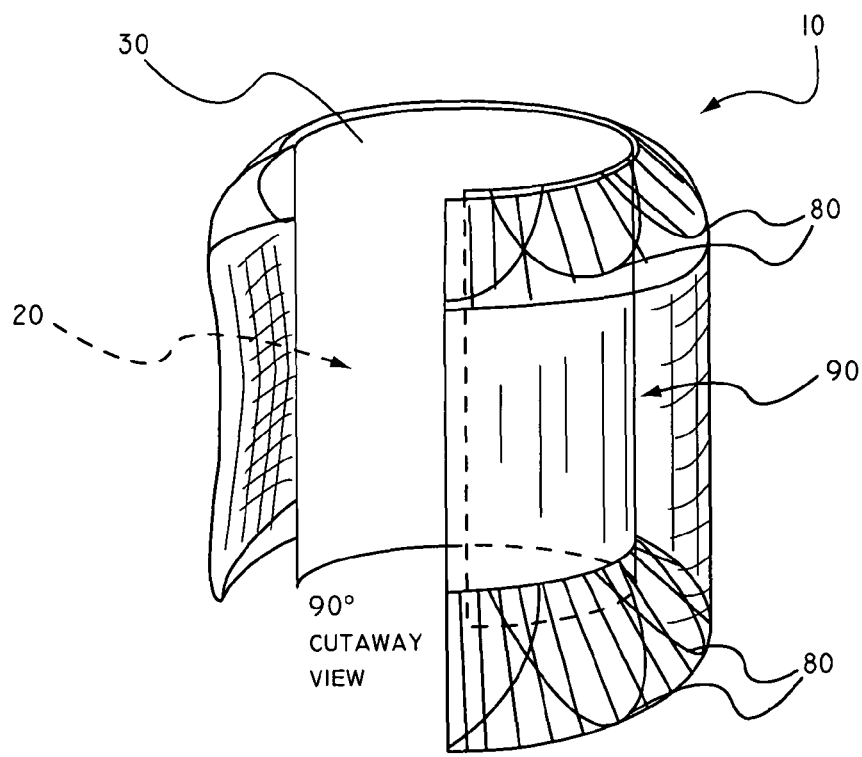
FIG. 23 illustrates another alternative embodiment of the grasping elements and seal of FIG. 21.
Figure 24:
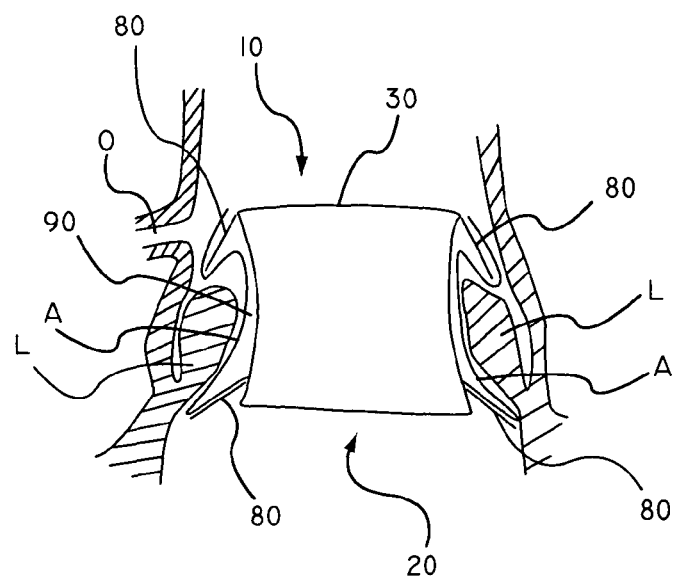
FIG. 24 illustrates the apparatus of FIG. 23 deployed across a patient's native valve.

FIG. 23 illustrates another alternative embodiment wherein seal 90 covers both the proximal and distal grasping elements and extends between the elements. The seal forms a tubular seal structure exterior to the body or braid of anchor 30 which can conform and seal against paravalvular leaks. FIG. 24 illustrates seal 90 of FIG. 23 deployed across a patient's native valve. The proximal grasping elements grasp the valve leaflets L and resist distal migration, while the distal grasping elements grasp the valve annulus A and resist proximal migration. Tissue grasping with grasping elements 80 preferably is atraumatic. As seen in FIG. 24, apparatus 10 is positioned distal of coronary ostia O, and seal 90 prevents or reduces blood flow around the replacement valve apparatus.

FIG. 25 is an embodiment of apparatus 10 comprising grasping elements 80 that are attached to anchor 30, rather than being formed integrally with the anchor, is described. In FIG. 25, grasping elements 80 comprise wires 82, as well as wire crimps 84 that attach the wires to the anchor. Each grasping element 80 comprises a wire 82 that optionally may be interwoven with the braid of anchor 30. Each end of each wire 82 is attached to the braid of anchor 30 via a crimp 84. The spacing about the circumference of the anchor between the ends of each wire forms an atraumatic grasping element 80. A plurality of such grasping elements are formed about the circumference of the anchor to facilitate circumferential grasping of tissue.

In FIG. 25, grasping elements 80 are attached to anchor 30 in a manner such that adjacent grasping elements partially overlap one another. The degree of overlap may be varied, as desired. Alternatively, the grasping elements may be attached such that there is no overlap between adjacent grasping elements.

Each crimp 84 of FIG. 25 has a first end that crimps to a wire 82 and a second end that crimps to the braid of anchor 30. In this configuration, each grasping element requires two unique crimps 84 for attachment to the braid. With reference to FIG. 26, an alternative crimp 85 for attaching the grasping elements to the anchor is described that reduces the total number of crimps required to attach a given number of grasping elements 80 to anchor 30. Each crimp 85 comprises a central section 86 that crimps onto the anchor, a first end 87a that crimps onto a first wire 82 and a second end that crimps onto a second wire 82. Thus, crimps 85 are shared between adjacent grasping elements 80, thereby reducing the number of crimps needed to attach the grasping elements. In FIG. 26, adjacent grasping elements illustratively do not overlap, but it should be understood that overlapping grasping elements alternatively may be provided, as in FIG. 25.

In any of the embodiments of engagement or grasping elements described herein, the elements may have a different cross-sectional profile than that of the material from which the body of the anchor is fabricated, e.g., from that of the wires forming the braid of anchor 30. Additionally or alternatively, the grasping elements may be fabricated of different materials than those from which the anchor is fabricated and/or from which other grasping elements are fabricated. In FIG. 26, wires 82 forming grasping elements 80 illustratively have larger cross-sectional diameters than the cross-sectional diameter of the wire(s) forming the braid of anchor 30. This may, for example, make the wires forming grasping elements 80 stiffer than the wire(s) forming the braid of anchor 30.

Figure 27A:
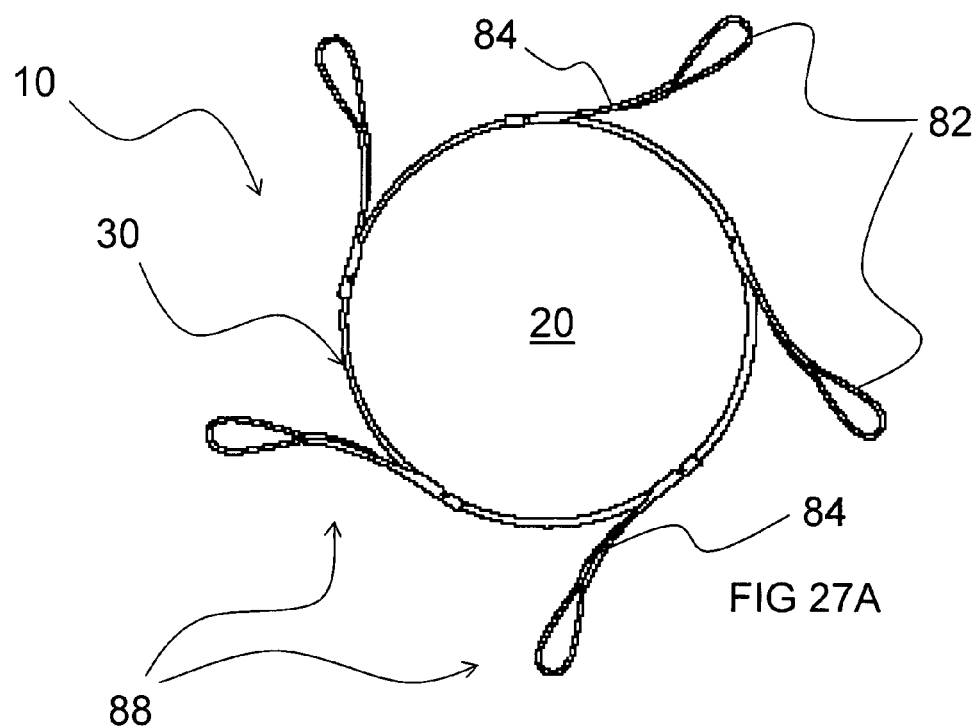
FIGS. 27A-27B illustrate additional, alternative attached grasping elements.
Figure 27B:
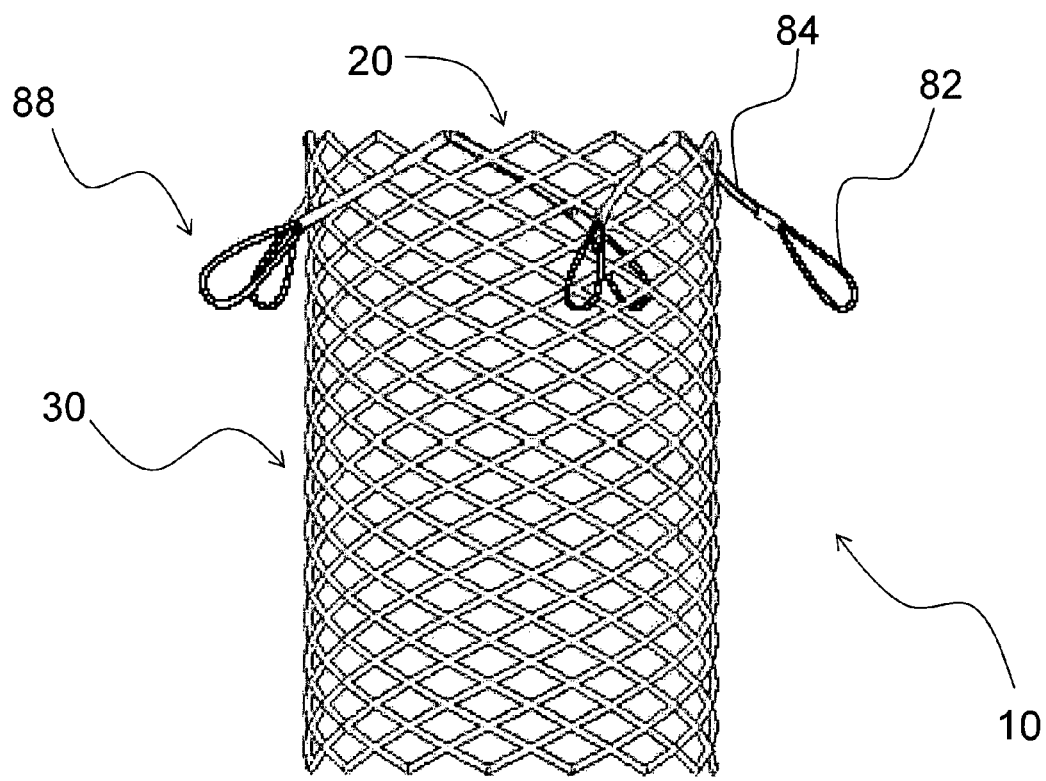

Referring now to FIG. 27, alternative attached grasping elements 88 are described. Each grasping element 88 is only attached to anchor 30 at a single location. Each grasping element 88 comprises a wire 82 that is formed into a loop. The two ends of the loop are crimped within a first end of a crimp 84. The other end of the crimp is crimped onto the anchor. By forming each wire 82 into a loop, an atraumatic grasping element 88 is formed for tissue grasping without necessitating attachment of the grasping element to the anchor at multiple locations about the circumference of the anchor.

Although the grasping elements of FIGS. 25-27 have been attached to anchor 30 via crimping, it should be understood that any alternative or additional attachment technique may be utilized. For example, the grasping elements may additionally or alternatively be attached via interweaving with the braid and/or via welding soldering, wire wrapping, or other suitable attachment means. Additional attachment techniques within the scope of the present invention will be apparent to those of skill in the art.

In any of the embodiments described herein, the engagement or grasping elements or the step of engaging/grasping the tissue may provide a locating function for properly placing the apparatus. This locating function may be accomplished without necessitating a precise placement of the replacement valve, especially in embodiments that comprise both proximal and distal grasping elements, e.g., that grasp both the valve leaflets and the valve annulus. This locating function advantageously may be accomplished without necessitating tactile feedback regarding the positioning of the replacement valve.

While preferred embodiments of the present invention are shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus for endovascularly replacing a patient's heart valve having native leaflets, the apparatus comprising:
   an expandable anchor supporting a valve, the anchor and valve being adapted for percutaneous delivery and deployment, the anchor having a proximal end, a distal end, a longitudinal axis, and an outer surface, the anchor braided from a shape memory material, the anchor being expandable from a collapsed delivery configuration to a fully deployed configuration; and leaflet engagement elements are attached to the anchor, the leaflet engagement elements extending distally from the anchor at a location proximal of the distal end of the anchor in both the collapsed delivery configuration and the fully deployed configuration, the leaflet engagement elements extending over at least a portion of the outer surface of the anchor, wherein, when the anchor is in the collapsed delivery configuration, the leaflet engagement elements are parallel to the longitudinal axis of the anchor; and when the anchor is in the fully deployed configuration, the leaflet engagement elements are adapted to sandwich the native leaflets between the leaflet engagement elements and the anchor.

2. The apparatus of claim 1 wherein the leaflet engaging elements extend distally from the proximal end of the anchor.

3. The apparatus of claim 1 wherein, in the collapsed delivery configuration, the leaflet engagement elements lie against the outer surface of the anchor.

4. The apparatus of claim 1 wherein the anchor has an at-rest configuration between the collapsed delivery configuration and the fully deployed configuration, and, in the at-rest configuration, the leaflet engagement elements are positioned at a first angle relative to the outer surface of the anchor.

5. The apparatus of claim 4 wherein, in the fully deployed configuration, the leaflet engagement elements are positioned at a second angle relative to the outer surface of the anchor, the second angle being greater than the first angle.

6. The apparatus of claim 4, wherein the anchor in the at-rest configuration has a diameter larger than a diameter of the anchor in the collapsed delivery configuration and smaller than a diameter of the anchor in the fully deployed configuration.

7. The apparatus of claim 4, wherein the anchor is adapted to self-expand from the collapsed delivery configuration to the at-rest configuration and the anchor is adapted to actively expand from the at-rest configuration to the fully deployed configuration.

8. The apparatus of claim 1 wherein the leaflet engagement elements are integral with the anchor.

9. The apparatus of claim 1, wherein the apparatus is configured for resheathing upon deployment from a delivery sheath.

* * * * *